United States Patent
Galbo et al.

(10) Patent No.: US 8,367,743 B2
(45) Date of Patent: Feb. 5, 2013

(54) ADHESION PROMOTING PHOTOINITIATORS FOR UV CURED COATINGS OVER METAL SURFACES

(75) Inventors: James P. Galbo, Wingdale, NY (US); Ying Dong, Tarrytown, NY (US); Dante A. Galan, Corona, NY (US); Eugene V. Sitzmann, Newark, DE (US)

(73) Assignee: BASF SE, Ludwigshafen (DE)

( * ) Notice: Subject to any disclaimer, the term of this patent is extended or adjusted under 35 U.S.C. 154(b) by 995 days.

(21) Appl. No.: 12/288,062

(22) Filed: Oct. 16, 2008

(65) Prior Publication Data

US 2009/0104464 A1    Apr. 23, 2009

Related U.S. Application Data

(60) Provisional application No. 60/999,361, filed on Oct. 17, 2007.

(51) Int. Cl.
*B32B 15/08* (2006.01)
*B32B 27/00* (2006.01)
*G03F 7/031* (2006.01)
*A61K 6/083* (2006.01)

(52) U.S. Cl. .......... 522/8; 522/18; 522/20; 522/42; 522/43; 428/461

(58) Field of Classification Search ........... 522/8, 18, 522/20, 42, 43; 428/461
See application file for complete search history.

(56) References Cited

U.S. PATENT DOCUMENTS

| | | | |
|---|---|---|---|
| 4,861,916 A | 8/1989 | Köhler et al. | 568/337 |
| 5,045,573 A | 9/1991 | Köhler et al. | 522/42 |
| 5,256,446 A * | 10/1993 | Bogen | 427/163.4 |
| 5,532,112 A | 7/1996 | Köhler et al. | 430/281.1 |
| 5,776,658 A | 7/1998 | Niesert et al. | 430/281.1 |
| 5,942,290 A * | 8/1999 | Leppard et al. | 427/510 |
| 6,211,262 B1 * | 4/2001 | Mejiritski et al. | 522/71 |
| 6,251,962 B1 | 6/2001 | Desobry | 522/18 |
| 7,001,644 B2 * | 2/2006 | Baudin et al. | 427/508 |
| 7,084,183 B2 | 8/2006 | Fuchs et al. | 522/36 |
| 7,642,296 B2 * | 1/2010 | Husler et al. | 522/6 |
| 2002/0122872 A1 | 9/2002 | Leukel et al. | 427/2.1 |
| 2004/0034115 A1 | 2/2004 | Baudin et al. | 522/33 |
| 2004/0204521 A1 | 10/2004 | Camenzind et al. | 524/90 |
| 2006/0270748 A1 | 11/2006 | Sommerlade et al. | 522/6 |
| 2009/0087671 A1 * | 4/2009 | Millero et al. | 428/461 |
| 2010/0104979 A1 * | 4/2010 | Dietliker et al. | 430/281.1 |

FOREIGN PATENT DOCUMENTS

EP    0281941    3/1988

OTHER PUBLICATIONS

G.C. Simmons, "Studies on the Adhesion of Radiation Cured Coatings to metal Substrates." SURCOM Birmingham, Oct. 6-7, 1999, p. 1.
A. Mejiritski et al., "Development of Corrosion Resistant Energy Curable Coatings." RadTech Report, Jul./Aug. 2006, p. 13.
I.V. Khudyakov et al.,"New Developments in UV-Curable Urethane Acrylate Coatings," in RadTech e/5 2004 Technical Proceedings.
English language abstract for CN 1727321, Feb. 1, 2006.
English language abstract for DE 19700064, Jul. 17, 1997.
English language abstract for JP 2004010534, Jan. 15, 2004.
English language abstract for JP 10087566, Apr. 7, 1998.
English language abstract for JP 10017688, Jan. 20, 1998.
English language abstract for JP 9077891, Mar. 25, 1997.
English language abstract for JP 9328522, Dec. 22, 1997.

* cited by examiner

*Primary Examiner* — Nathan M Nutter
(74) *Attorney, Agent, or Firm* — Tyler A. Stevenson; Qi Zhuo; Joseph Suhadolnik

(57) ABSTRACT

Compounds containing both photoinitiator moieties and adhesion promoting moieties and coating formulations containing them are disclosed, in particular, durable UV cured primer layers for coil coatings. One embodiment includes a coated metal surface which comprises a metal substrate with at least one surface immediately adjacent to a coating layer comprising a photoinitiator chemically bound to an adhesion promoter is disclosed.

6 Claims, No Drawings

ADHESION PROMOTING PHOTOINITIATORS FOR UV CURED COATINGS OVER METAL SURFACES

This application claims benefit under 35 USC 119(e) of U.S. provisional application No. 60/999,361, filed Oct. 17, 2007, the disclosure of which is incorporated herein in its entirety by reference.

Compounds that contain both photoinitiator moieties and adhesion promoting moieties are provided which are used to generate a more durable UV cured primer layer for coatings over metal applications, for example, UV cured coil coatings. Also provided are coating compositions which comprise said compounds and an ethylenically unsaturated species, such as an acrylate resin or monomer, and optionally binder polymers and other components. For example, a coated metal surface which comprises a metal substrate with at least one surface immediately adjacent to a coating layer comprising a photoinitiator chemically bound to an adhesion promoter is disclosed.

UV cured coil coatings offer energy saving advantages over conventional thermally cured systems by making it possible to use very high line speeds at ambient temperature. While thermal curing may use a dwell time of 30 seconds in a 280 degree Celsius oven, UV curing can occur in one second as the coating formulation passes under a lamp at high speed. From an environmental perspective, UV cured coil coatings use much less solvent than conventional thermally cured resins.

Coil coating involves the application of an organic resin to a flat metal surface. The metal is, for example, aluminum or steel. In the process, a coil of metal is unwound, cleaned, treated, primed, cured, treated with a top coat, cured and rewound. When the metal roll reaches the customer, it is uncoiled and fashioned into the end product. The end product is, for example, a roof or building facade, office furniture, filing cabinets, appliances, or the hood or door of a car. The severe stress that is placed upon the coil coating as it is rolled for storage and shipment, then flattened, cut, shaped, and fastened requires that the coating be durable. Durability is also required throughout the lifetime of the metal object, which may be in an outdoor application exposed to moisture, sunlight, and various chemicals in the atmosphere. Excellent adhesion of the primer layer, which is a clear or slightly pigmented resin, is vital to acceptable performance of coatings over metal during manufacture and throughout the usable lifetime of the end product.

In spite of the advantages of using UV light to cure coil coatings, a major disadvantage with respect to thermal curing is reduced adhesion of the primer layer to the metal surface. This can be due to shrinkage of the resin during the rapid cure. Poor adhesion of the primer layer leads to corrosion and delamination, which will affect the long term performance of the top coat which is applied over the primer layer. See for example, G. C. Simmons, "Studies on the Adhesion of Radiation Cured Coatings to Metal Substrates." SURCOM Birmingham, Oct. 6-7, 1999, p. 1. and A. Mejritski, D. C. Neckers, et. al., "Development of Corrosion Resistant Energy-Curable Coatings." RadTech Report, July/August 2006, p. 13.

UV cured coil coating primers frequently comprise monomers, oligomers or resins containing ethylenic unsaturation, such as acrylates, and adhesion promoters and photoinitiators. The photoinitiator rapidly undergoes fragmentation during exposure to the UV light source, initiating polymerization reaction of the ethylenically unsaturated resin, for example, an acrylate resin. In order to ensure good adhesion to the metal surface, a sufficient amount of an adhesion promoting compound, typically a strong acid, is added to the formulation. The adhesion promoter, which has a chemical affinity for the metal surface, polymerizes with the resin and thereby anchors the cured primer layer to the metal surface.

CN 1727321 discloses the preparation of ketone derivatives having multiple hydrophilic groups and their use as photopolymerization and photocrosslinking catalysts.

DE 19700064 discloses photocurable thermotropic gels made from 2-hydroxy acetophenone photoinitiators that are derivatives of substituted alkylene or polyalkylene oxide containing a hydrophilic group such as carboxylic acid or hydroxyl.

JP 2004010534 discloses the reaction of an aromatic hydroxyketone, which can be substituted by hydroxypolyalkylene oxide, with a monocarboxylic acid having the maleimide group.

JP 10087566 discloses 2-butenoic monoester derivatives of 2-hydroxy-2-methylpropan-1-one used as photoinitiators in the manufacture of hard coatings.

JP 10017688, JP 09077891, and JP 09328522 describe improving adhesion and scratch resistance of a coating by grafting monomers using trialkoxysilyl urethane-substituted propiophenone photoinitiators.

US Pub. Appl. No. 2004/204521, incorporated herein in its entirety by reference, discloses the reaction of nano-scaled fillers with photoinitiators, such as 2-hydroxy propiophenone derivatives, functionalized with reactive groups including trialkoxy silanes, phosphonic acid, and phosphoric acid.

US Pub. Appl. No. 2002/122872, incorporated herein in its entirety by reference, discloses a process for coating a surface using 2-hydroxyacetophenone photoinitiator substituted on the aromatic ring by either alkylene, or alkylene or polyalkylene oxide terminated by hydroxyl or carboxylic acid.

U.S. Pat. No. 5,532,112, incorporated herein in its entirety by reference, discloses hydroxyl, carboxylic acid and trialkoxysilyl substituted 2-hydroxyacetophenone photoinitiators which can form bonds to the cured substrate, e.g., ethylenically unsaturated systems.

U.S. Pat. Nos. 4,861,916 and 5,045,573, incorporated herein in their entirety by reference, disclose carboxylic acid, hydroxyl, and hydroxyalkylamino substituted 2-hydroxyacetophenone photoinitiators for the polymerization of ethylenically unsaturated materials, especially in aqueous media.

U.S. Pat. No. 6,251,962, incorporated herein in its entirety by reference, discloses carboxylic and hydroxyl substituted 2-hydroxyacetophenone photoinitiators in high solids paint to obtain polymers with specific molecular weight and polydispersity.

US Pub. Appl. No. 2006/270748, incorporated herein in its entirety by reference, discloses methylenebis(carbonylphenyl) compounds containing alpha-hydroxy substituted alkyl groups and a hydroxyl substituted polyalkylene oxide or hydroxyalkylamino substituent for use in the cure of coatings and inks.

U.S. Pat. No. 7,084,183, incorporated herein in its entirety by reference, discloses difunctional photoinitiator compounds.

None of the aforementioned patents or publications teaches the synthesis or use of a compound which combines in the same compound a photoinitiator with an adhesion promoter for improved adhesion of a UV cured coating applied over a metal surface.

The present invention provides a coating formulation comprising a compound wherein an alpha hydroxy ketone photoinitiator is chemically bound to an adhesion promoter such as a carboxylic acid, a phosphonate, or a trialkoxy silane. The coating adheres strongly to metal surfaces and is effective as a primer for metals. One embodiment of the invention therefore provides a UV curable coil coating. In one particular embodiment, a primer layer for metal surfaces such as a primer used in coil coating applications is provided. Also provided are novel compounds comprising an alpha hydroxy ketone photoinitiator chemically bound to an adhesion promoter such as a carboxylic acid, a phosphonate, or a trialkoxy silane.

As the instant photoinitiators are chemically bonded to organic adhesion promoters, the primer layer formed during cure will be anchored to the metal surface. One can therefore add less of a separate adhesion promoter to the formulation, or even not add any additional adhesion promoter and still ensure that the polymerized resin is attached to the metal surface.

Because the instant compounds provide the advantage of reducing the amount of adhesion promoting compound required to obtain excellent adhesion, the use of larger concentrations of a separate adhesion promoting compound, which can adversely affect the properties of the primer layer and subsequently the topcoat, is not necessary. Furthermore, because the adhesion promoter anchors the photoinitiator to the metal surface, the fragments that results from Norrish type I cleavage of the photoinitiator are less likely to volatize from the formulation.

I. V. Khudyakov, T. G. Gantt, M. B. Purvis, and B. J. Overton, "New developments in UV-Curable Urethane Acrylate Coatings," in RadTech e/5 2004 Technical Proceedings, describe the use of oligomers with grafted photoinitiators and adhesion promoters that give superior properties to acrylate coatings applied over glass. Besides the different surface, the instant invention differs from the methodology described by Khudyakov et. al. in that the instant invention describes the preparation and use of a photoinitiator which is grafted to an adhesion promoter, but not to the coating, prior to the curing process. The instant photoinitiator-adhesion promoter combination is versatile because it is prepared independently of the oligomers used in the resin and can therefore be used in a variety of resin systems.

DESCRIPTION OF THE INVENTION

The present invention provides a coated metal surface which comprises
a) a metal substrate, for example steel or aluminum, with at least one surface which is immediately adjacent to a coating layer which coating layer comprises
b) one or more ethylenically unsaturated compounds, for example, mono- or polyunsaturated monomers, oligomers or prepolymers, for example acrylate monomers oligomers or prepolymers, and
c) from about 0.05 to about 25%, for example from about 0.1 to about 10%, for example from about 1 to about 5% by weight based on the total weight of the coating layer solids one or more compounds of the formulae:

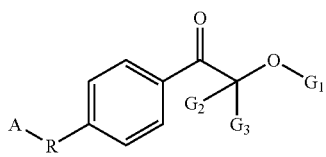

I

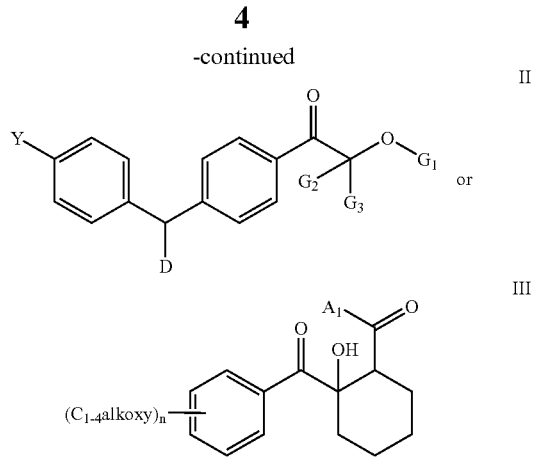

wherein
$G_1$ is —H, glycidyl, —CH$_2$—CH(OH)—CH—NR$_4$R$_6$, —CH(CH$_2$OH)—CH—NR$_4$R$_6$ or —CH$_2$—CH(OH)—CH—NR$_4$R$_6$,
$G_2$ and $G_3$ are, independently, $C_1$-$C_4$ alkyl, or taken together, pentamethylene,
R is $C_1$-$C_6$ alkylene, $C_1$-$C_6$ alkylene-oxy, $C_4$-$C_6$ alkylene interrupted by 1 or 2 oxygen atoms or $C_4$-$C_6$ alkene-oxy interrupted by 1 or 2 oxygen atoms
A is a group selected from —(O)$_s$—C(=O)G, —O—CH$_2$—C(=O)G, —(O)$_s$—P(=O)(OR$_2$)(OR$_3$), —(O)$_s$—Si(OR$_2$)$_2$OR$_3$,

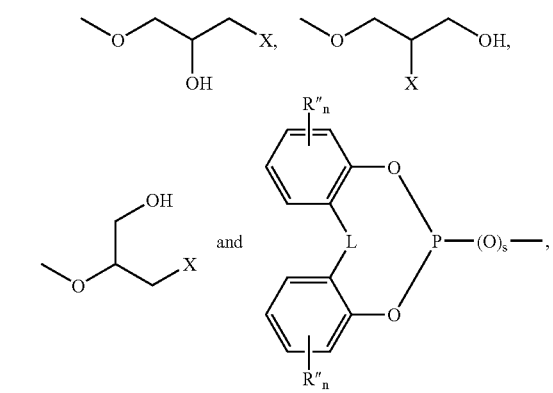

s is 0 or 1,
n is 0, 1 or 2
L is a direct bond, —CH$_2$— or —CH(CH$_3$)—,
G is selected from OH,

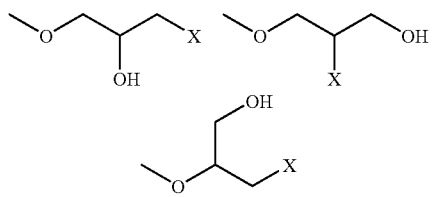

—NR$_4$—(CH$_2$)$_3$—Si(OR$_2$)$_2$OR$_3$,
—R$_7$—CH$_2$N(R$_8$)$_p$—(CH$_2$)$_3$—Si—(OR$_2$)$_2$OR$_3$,
—R$_{10}$—C(=O)—OH,
phenyl or naphthyl, each being substituted by one to three —COOH, or one or two —C(=O)—O—CH2-C(CH$_3$)

(CH₂OH)—COOH and, optionally by —(C=O)—O—Z or one or two —COO—R₁₁ or —COO—(R₄—O)ₓ—H, where R₄ is not —H, and x is 1-3;

phenyl or naphthyl, each being substituted by one or two —(C=O)—N(R₁₅)ₚ(R₁₆)₂₋ₚ and optionally substituted by —(C=O)—O—Z, where p is 0 or 1, R₁₅ is —H, C₁-C₄ alkyl, or —(CH₂)₃—Si(OR₂)₂OR₃, and R₁₆ is C₁-C₄ hydroxyalkyl or —(CH₂)₃—Si(OR₂)₂OR₃; and phenyl substituted at the 2 position by a group C(=O)OH and at the 4 or 5 position by a group

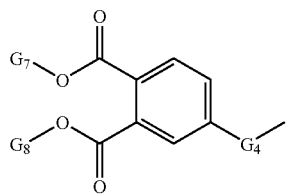

wherein

G₄ is a direct bond or —(C=O)—, one of G₇ or G₈ is —H, the other is —H, —Z, or —R₁₁, R₁₁ is C₁-C₄ alkyl, C₃-C₄ alkenyl, or C₃-C₆ alkyl interrupted by 1 or 2 —O—, and wherein R₁₁ is optionally substituted on a saturated carbon atom by —OH with the proviso that the substitution does not form an acetal X is
O—(CH₂)₃—Si(OR₂)₂OR₃,
—NR₄—(CH₂)₃—Si(OR₂)₂OR₃,
—N(R₅)ₚ(R₆)₂₋ₚ, p is 0 or 1, Z is

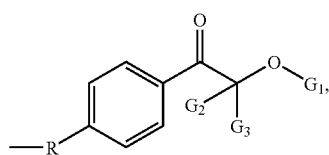

Y is —H or —(C=O)—C(G₁)(G₂)-OG₁,

R₂ and R₃ are, independently, —H or C₁-C₄ alkyl, or R₃ is —Z,

R₄ is —H or C₁-C₄ alkyl, or —(CH₂)₃—Si(OR₂)₂OR₃,

R₅ is —H, C₁-C₄ alkyl, —CH₂—CH(OH)—CH₂—O—Z, —CH(CH₂OH)—CH₂—O—Z, —CH₂—CH(OZ)-CH₂—OH, or —(CH₂)₃—Si—(OR₂)₂OR₃;

R₆ is C₁-C₄ alkyl substituted by OH or COOH, or R₆ is —(CH₂)₃—Si(OR₂)₂OR₃,

R₇ is —CH₂— or —CH(CH₃)—,

R₈ is —H, C₁-C₄ alkyl, —(CH₂)₃—Si—(OR₂)₂OR₃, —CH₂—R₇—(C=O)—O—Z, —CH₂—R₇—(C=O)—O—CH₃, —CH₂—R₇—(C=O)—O—CH₂CH₃;

R₉ is —(CH₂)₃—Si—(OR₂)₂OR₃ where R₂ and R₃ are methyl or ethyl,

R₁₀ is C₂-C₆ alkylene, alkenylene, or alkylene substituted by —(CH₂)₃—Si(OR₂)₂OR₃, or R₁₀ is norbornylene, D is AR— or

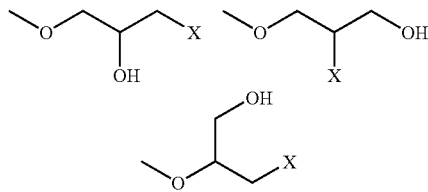

—O—C(=O)—NR₄—(CH₂)₃—Si(OR₂)₂OR₃,
—O—(C=O)—R₇—CH₂N(R₈)ₚ(R₉)₂₋ₚ, p is 0 or 1
—O—C(=O)—R₁₀—C(=O)—OH,

A₁ is —OH, or —NR₁₂R₁₃, where R₁₂ is —H, C₁-C₄ alkyl, C₁-C₄ alkyl substituted by —OH or —COOH, or —(CH₂)₃—Si—(OR₂)₂OR₁₄, where R₁₄ is —H or C₁-C₄ alkyl, and R₁₃ is C₁-C₄ alkyl substituted by —OH or —COOH, or R₁₃ is —(CH₂)₃—Si—(OR₂)₂OR₁₄.

Alkyl is straight or branched chain of the specified number of carbon atoms, for example, methyl, ethyl, n-propyl, n-butyl, sec-butyl, tert-butyl, n-hexyl, n-octyl, 2-ethylhexyl, n-nonyl, n-decyl, n-undecyl, n-dodecyl.

Alkylene is a chain of the specified number of carbon atoms substituted at each terminus as indicated. A branched chain alkylene may also be present and is a branched carbon chain substituted at two termini as indicated. Alkylene includes, for example, methylene, ethylene, propylene, butylene, methylpropylene, dimethylethylene, hexylene, octylene, 2-ethylhexylene, nonylene, decylene, undecylene, dodecylene.

Also provided are new compounds of formula I, II or III which are very effective as compounds of component c) in the coatings above. The novel compounds are compounds of formula I, II or III above wherein R is C₁-C₆ alkylene, C₂-C₆ alkylene-oxy, C₄-C₆ alkylene interrupted by 1 or 2 oxygen atoms, or C₄-C₆ alkylene-oxy interrupted by 1 or 2 oxygen atoms or AR— taken together is a group —O—CH₂—C(=O)G, —O—CH₂—P(=O)(OR₂)(OR₃),
—O—CH₂—Si(OR₂)₂OZ, or

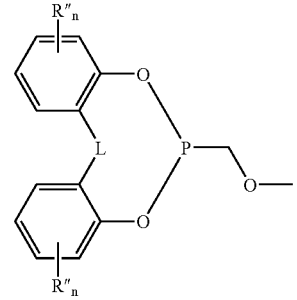

With the proviso that in Formula (I)

A is not —P(=O)(OH)₂ or —Si(OR₂)₂OR₃, unless R₃ is Z; and also in Formula (I) AR is not
—O—(CH2)₁₋₆-COOH,       —(CH₂)₁₋₆—COOH,
—O—(CH₂)₁₋₆—O—CH₂—COOH, —(CH₂)₁₋₆—O—CH₂—COOH,
O—(CH₂)₂—O—Si(OR₂)₂OR₃, unless R₃ is Z,
O—(CH₂)₂—O—C(=O)—NR₄—(CH₂)₃—Si(OR₂)₂OR₃, unless R₃ is Z
—O—C(=O)—R₁₀—C(=O)—OH when R is alkylene-oxy or alkylene-oxy interrupted by oxygen atoms and R₁₀ is —CH$_2$CH$_2$—, —CH═CH—, or —CH═CH— substituted by once or twice by —CH$_3$, or —O—C(═O)—R$_{10}$—C(═O)—OH when R is alkylene or alkylene interrupted by oxygen atoms and R$_1$ and R$_{10}$ combined contain up to 8 saturated carbon atoms;

in Formula (II)

when Y is —(C═O)—C(G$_1$)(G$_2$)-OH, D is not —O—C(═O)—NR$_4$—(CH$_2$)$_3$—Si(OR$_2$)$_2$OR$_3$ where R$_4$ is —H or C$_1$-C$_4$ alkyl, unless R$_3$ is —Z.

and in formula (III)

A$_1$ is not —COOH, or —NR$_{12}$R$_{13}$ where R$_{12}$ is —H and R$_{13}$ is —(CH$_2$)$_3$—Si—(OR$_2$)$_2$OR$_3$, except where R$_3$ is —Z.

For example, novel and effective compounds are compounds of formula I, II or III above, wherein G$_1$ is H, G$_2$ and G$_3$ are each methyl, R is C$_2$-C$_6$ alkylene or C$_2$-C$_6$ alkylene-oxy, A is a group selected from —O—C(═O)G, —C(═O)G, —O—(CH$_2$)$_2$—C(═O)G,

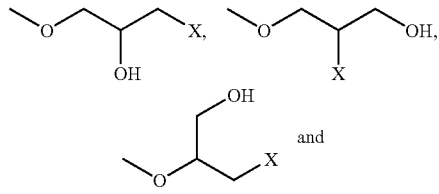

and

G is selected from
—NR$_4$—(CH$_2$)$_3$—Si(OR$_2$)$_2$OR$_3$, R$_4$ is —H or C$_1$-C$_4$ alkyl, or —(CH$_2$)$_3$—Si(OR$_2$)$_2$OR$_3$,
—R$_7$—CH$_2$N(R$_8$)$_p$—(CH$_2$)$_3$—Si—(OR$_2$)$_2$OR$_3$, R$_8$ is —H, C$_1$-C$_4$ alkyl, —(CH$_2$)$_3$—Si(OR$_2$)$_2$OR$_3$, —CH$_2$—R$_7$—(C═O)—O—Z, —CH$_2$—R$_7$—(C═O)—O—CH$_3$, —CH$_2$—R$_7$—(C═O)—O—CH$_2$CH$_3$; R$_7$ is —CH$_2$— or —CH(CH$_3$)—,
—R$_{10}$—C(═O)—OH, R$_{10}$ is C$_2$-C$_6$ alkylene, alkenylene, or alkylene substituted by —(CH$_2$)$_3$—Si(OR$_2$)$_2$OR$_3$, or R$_{10}$ is norbornylene,
phenyl substituted by two —COOH, and, optionally by —(C═O)—O—Z;
phenyl, substituted by —(C═O)—N(R$_{15}$)$_p$(R$_{16}$)$_{2-p}$ and optionally substituted by —(C═O)—O—Z,
where p is 0 or 1, R$_{15}$ is —H, C$_1$-C$_4$ alkyl, or —(CH$_2$)$_3$—Si(OR$_2$)$_2$OR$_3$, and R$_{16}$ is C$_1$-C$_4$ hydroxyalkyl or —(CH$_2$)$_3$—Si(OR$_2$)$_2$OR$_3$;
X is —NR$_4$—(CH$_2$)$_3$—Si(OR$_2$)$_2$OR$_3$, R$_4$ is —H or C$_1$-C$_4$ alkyl, or —(CH$_2$)$_3$—Si(OR$_2$)$_2$OR$_3$, —N(R$_5$)$_p$(R$_6$)$_{2-p}$, p is 0 or 1, R$_5$ is —H, C$_1$-C$_4$ alkyl, —CH$_2$—CH(OH)—CH$_2$—O—Z, —CH(CH$_2$OH)—CH$_2$—O—Z, or —(CH$_2$)$_3$—Si—(OR$_2$)$_2$OR$_3$; R$_6$ is C$_1$-C$_4$ alkyl substituted by OH or COOH, or R$_6$ is —(CH$_2$)$_3$—Si(OR$_2$)$_2$OR$_3$;

and in Structure (II), when Y is H, D is —(CH$_2$)$_{1-6}$COOH, —O—C(═O)—NR$_4$—(CH$_2$)$_3$—Si(OR$_2$)$_2$OR$_3$, where R$_4$ is —H or —(CH$_2$)$_3$—Si(OR$_2$)$_2$OR$_3$, R$_2$ is methyl or ethyl, and R$_3$ is —H, methyl, or ethyl, or —O—CH$_2$—CH(OH)—CH$_2$—N(R$_5$)(R$_6$), wherein R$_5$ is H and R$_6$ is —(CH$_2$)$_3$—Si—(OR$_2$)$_2$OR$_3$ or C$_2$-C$_4$ alkyl substituted by —OH or each of R$_5$ and R$_6$ is —(CH$_2$)$_3$—Si(OR$_2$)$_2$OR$_3$ or C$_2$-C$_4$ alkyl substituted by —OH and when Y is —(C═O)—C(CH$_3$)$_2$—OH, D is —O—CH$_2$—CH(OH)—CH$_2$—N(R$_5$)(R$_6$), wherein R$_5$ is H and R$_6$ is —(CH$_2$)$_3$—Si—(OR$_2$)$_2$OR$_3$ or C$_2$-C$_4$ alkyl substituted by —OH or each of R$_5$ and R$_6$ is —(CH$_2$)$_3$—Si(OR$_2$)$_2$OR$_3$ or C$_2$-C$_4$ alkyl substituted by —OH and In Structure (III), A$_1$ is —NR$_{12}$R$_{13}$ where R$_{12}$ and R$_{13}$ are each —CH$_2$CH$_2$—OH or R$_{12}$ is H and R$_{13}$ is —CH$_2$CH$_2$—OH or —CH$_2$CH$_2$CH$_2$—OH.

For example, a compound of the formula

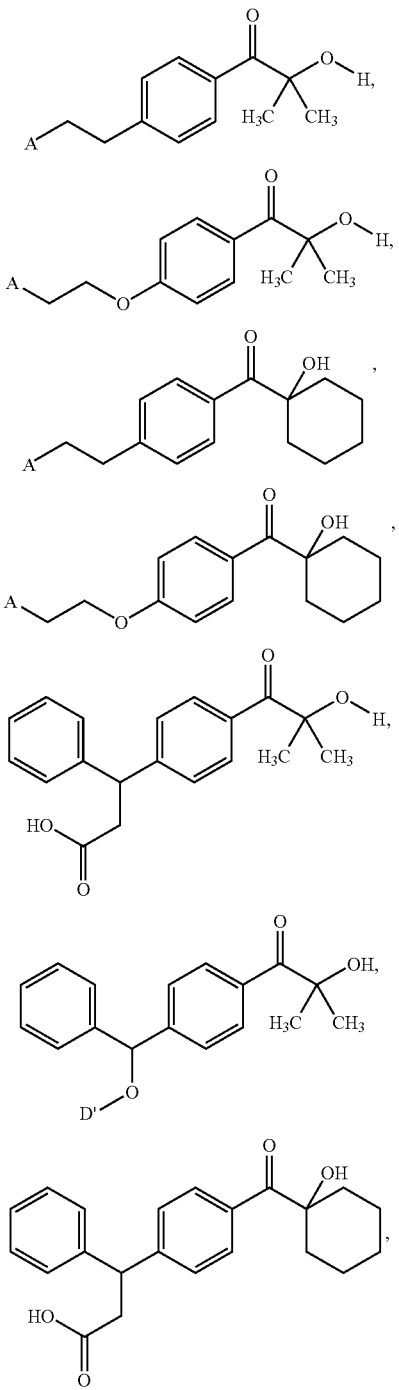

-continued

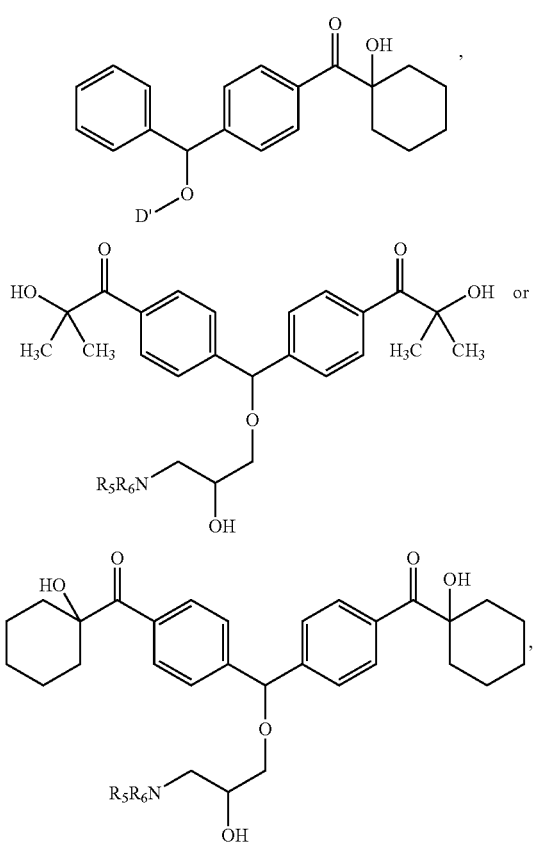

wherein
A is —O—CH$_2$—CH(OH)—CH$_2$—N(CH$_2$CH$_2$OH)$_2$, —O—C(=O)—R$_{10}$—C(=O)—OH, R$_{10}$ is —CH$_2$CH$_2$— substituted by either —(CH$_2$)$_3$—Si—(OCH$_3$)$_3$ or —(CH$_2$)$_3$—Si—(OCH$_2$CH$_3$)$_3$, —O—(C=O)—R$_7$—CH$_2$N(R$_8$)(R$_9$), R$_8$ is —CH$_2$—R$_7$—(C=O)—O—Z where R$_7$ is —CH$_2$—, R$_9$ is —(CH$_2$)$_3$—Si—(OR$_2$)$_2$OR$_3$ where R$_2$ and R$_3$ are methyl or ethyl, or A is —O—(C=O)—R$_7$—CH$_2$N(R$_8$)(R$_9$), R$_8$ is —CH$_2$—R$_7$—(C=O)—O—CH$_3$ or —CH$_2$—R$_7$—(C=O)—O—CH$_2$CH$_3$, where R$_7$ is —CH$_2$—,
R$_9$ is —(CH$_2$)$_3$—Si—(OR$_2$)$_2$OR$_3$ where R$_2$ is methyl or ethyl and R$_3$ is —Z, D' is —C(=O)—NR$_4$—(CH$_2$)$_3$—Si(OR$_2$)$_2$OR$_3$, where R$_4$ is —H or —(CH$_2$)$_3$—Si(OR$_2$)$_2$OR$_3$, R$_2$ is methyl or ethyl, and R$_3$ is —H, methyl, or ethyl, or
—CH$_2$—CH(OH)—CH$_2$—N(R$_5$)(R$_6$), R$_5$ is H and R$_6$ is —(CH$_2$)$_3$—Si—(OR$_2$)$_2$OR$_3$ or C$_2$-C$_4$ alkyl substituted by —OH or each of R$_5$ and R$_6$ is —(CH$_2$)$_3$—Si(OR$_2$)$_2$OR$_3$ or C$_2$-C$_4$ alkyl substituted by —OH:

for example a compound of the formula

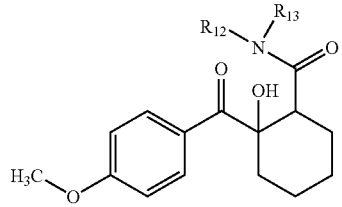

wherein R$_{12}$ and R$_{13}$ are each —CH$_2$CH$_2$—OH or R$_{12}$ is H and R$_{13}$ is —CH$_2$CH$_2$—OH or —CH$_2$CH$_2$CH$_2$—OH
or, for example,
a compound of the formula

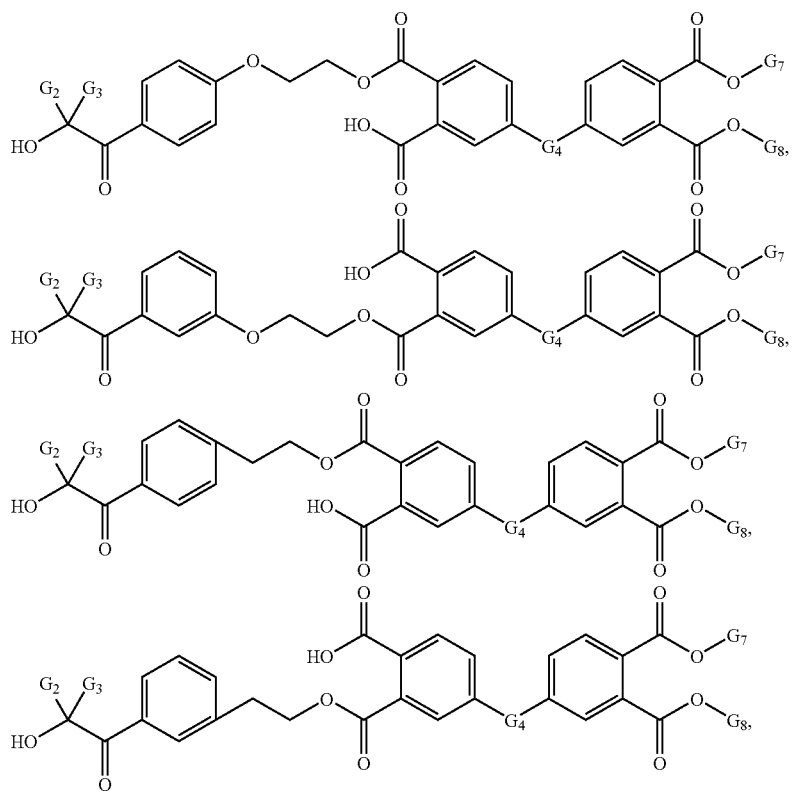

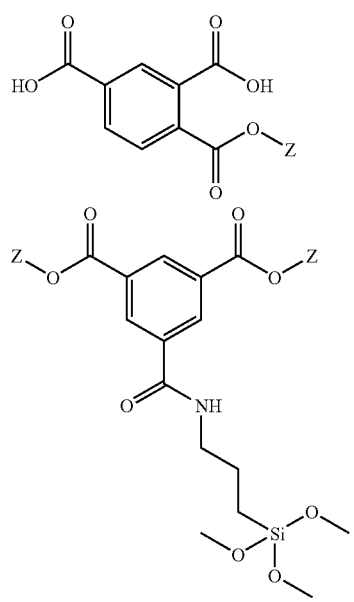
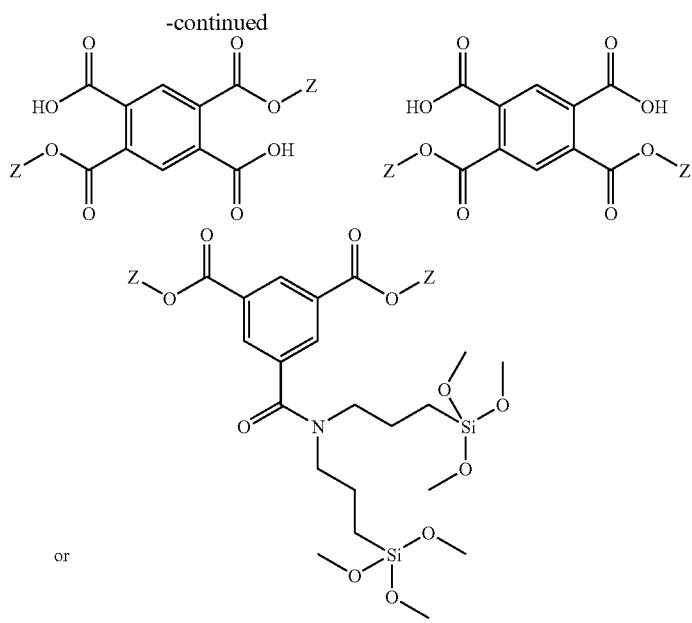

wherein
Z is

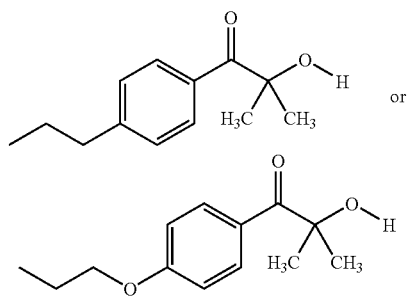

$G_2$ and $G_3$ are methyl or taken together, pentamethylene,
$G_4$ is a direct bond or —(C=O)—,
and one of $G_7$ or $G_8$ is —H, the other is —H or —Z.

The photoinitiators of the invention shown above comprise phenyl rings that are typically ortho- or para-substituted, for example, the compounds of formula I or II. It should be obvious to the organic chemist that the synthetic methods known and/or described herein for preparing such aromatic moieties often generate meta-substituted materials as minor components. As a result, in many cases, these minor products will also be present along with the claimed materials.

The coating layer of the invention may further comprise about 1 to about 25, for example about 5 to about 25 weight percent based on total solids, of an additional photoinitiator or photoinitiator blend. For example, the additional photoinitiator or photoinitiator blend comprises one or more compounds selected from phenyl bis(2,4,6-trimethylbenzoyl)phosphine oxide, 2-hydroxy-2-methyl-1-phenyl-1-propanone, 2-Hydroxy-1-{4-[4-(2-hydroxy-2-methylpropionyl)benzyl]phenyl}-2-methylpropan-1-one, 2-Hydroxy-1-[4-(2-hydroxyethoxy)phenyl]-2-methylpropan-1-one,benzophenone and 1-hydroxycyclohexyl phenyl ketone.

For example, the additional photoinitiator or photoinitiator blend comprises one or more compounds or blends selected from a blend of 20% by weight phenyl bis(2,4,6-trimethylbenzoyl) phosphine oxide and 80% by weight 2-hydroxy-2-methyl-1-phenyl-1-propanone;
2-Hydroxy-1-{4-[4-(2-hydroxy-2-methylpropionyl)benzyl] phenyl}-2-methylpropan-1-one;
2-Hydroxy-1-[4-(2-hydroxyethoxy)phenyl]-2-methylpropan-1-one;
a blend of 50 weight % benzophenone and 50 weight % 1-hydroxycyclohexyl phenyl ketone;
phenyl bis(2,4,6-trimethylbenzoyl)phosphine oxide;
1-Hydroxycyclohexyl phenyl ketone;
and 2-Hydroxy-2-methyl-1-phenyl propan-1-one:

for example, the additional photoinitiator or photoinitiator blend comprises the blend 50 weight % benzophenone and 50 weight % 1-hydroxycyclohexyl phenyl ketone or the compound phenyl bis(2,4,6-trimethylbenzoyl)phosphine oxide.

The compounds formula I, II or III may be prepared by the functionalization of photoinitiator molecules using standard synthetic methodology. Photoinitiator starting materials not commercially available may be synthesized by Friedel-Crafts acylation of the appropriate hydrocarbon, followed by bromination and hydrolysis, according to the methodology of U.S. Pat. No. 5,045,573, incorporated herein in its entirety by reference. In some cases, it is possible to start with a hydrocarbon that already contains the attached adhesion promoter, which may be in a protected form, such as 3,3-diphenylpropionic acid methyl ester, and subsequently build up the photoinitiator using Friedel-Crafts chemistry.

Glycidyl ether derivatives of hydroxyl substituted photoinitiators, which may be prepared according to the method described in U.S. Pat. No. 5,532,112 or U.S. Pat. No. 5,837,746, incorporated herein in their entirety by reference, can be reacted with an amine substituted by hydroxyalkyl or trialkoxysilylalkyl to form beta-amino alcohols further substituted by hydroxyl or trialkoxysilyl groups by adapting the methodology described in *Industrial and Engineering Chemistry*, 1956, 48, 94-97. The reaction of carboxylic acid substituted photoinitiators with commercially available trialkoxysilylpropyl glycidyl ethers, which is adapted from the procedure in *Industrial and Engineering Chemistry*, 1956, 48, 86-93, forms carboxylic acid esters having trialkoxysilyl substituents Trialkoxysilylalkyl amides may be synthesized from the reaction of commercially available isocyanato substituted trialkoxysilanes with hydroxyl substituted photoinitiators by using the methodology described in "A Selective Catalyst for Two Component Waterborne Polyurethane Coatings," *International Waterborne, High-solids, and Powder coatings Symposium*, Feb. 10-12, 1999, New Orleans, La.

Trialkoxysilyl derivatives may also be synthesized by the Michael reaction of commercially available trialkoxysilylalkyl substituted amine with methyl acrylate or methyl methacrylate, using methodology described in U.S. Pat. No. 4,558,120, incorporated herein in its entirety by reference, followed by transesterification with alkoxy substituted photoinitiators.

Another method to introduce trialkoxysilyl substituents is the hydrosilation of ethylenically unsaturated derivatives of photoinitiators, such as those prepared in U.S. Pat. Nos. 5,532,112 or 5,837,746, with trialkoxysilanes catalyzed by rhodium(II) complexes, as described in *J. Organometal. Chem.*, 1981, 208, 401-406.

The use of trialkoxysilane reagents often results in exchange reactions with alcohol solvents used in the reactions or with hydroxyl substituted photoinitiators such as 4'-(2-hydroxyethoxy)-2-hydroxy-2-methylpropiophenone.

Carboxylic acid derivatives may be formed by reaction of carboxylic acid anhydrides with hydroxyl substituted photoinitiators. The reaction may be catalyzed by 4-dimethylaminopyridine as described in *J. Org. Chem.*, 1984, 49, 458-468. The anhydride may be substituted by triethoxysilylalkyl. Another option is the reaction of hydroxy substituted photoinitiators with an excess of a di-acyl or tri-acyl substituted carboxylic acid compound. The reaction may be catalyzed by pyridine. The unreacted acyl chloride substituents are then converted to carboxylic acids by hydrolysis.

The reaction of halogenated photoinitiators with trialkyl phosphites, as described in *Chem. Rev.*, 1981, 81, 415-430, gives dialkyl phosphonate derivatives.

2-Hydroxy-2-benzoyl substituted cyclohexanecarboxylic acid derivatives are formed from 6-benzoyl- or substituted 6-benozyl-7-oxa-bicyclo[4.2.0]octan-8-one by hydrolysis or reaction with an amine substituted by hydroxyl or trialkoxylsilylalkyl.

The ethylenically unsaturated compounds (b) of the coating formulation typically contain one or more olefinic double bonds. They may be low molecular weight (monomeric) or higher molecular weight (oligomeric), see e.g., U.S. Pat. No. 7,084,183, already incorporated by reference.

Examples of monomers having a double bond are alkyl and hydroxyalkyl acrylates and methacrylates, e.g. methyl, ethyl, butyl, 2-ethylhexyl and 2-hydroxyethyl acrylate, isobornyl acrylate, and methyl and ethyl methacrylate. Further examples are acrylonitrile, acrylamide, methacrylamide, N-substituted(meth)acrylamides, vinyl esters, such as vinyl acetate, vinyl ethers, such as isobutyl vinyl ether, styrene, alkyl- and halo-styrenes, N-vinylpyrrolidone, vinyl chloride and vinylidene chloride.

Examples of monomers having a plurality of double bonds are ethylene glycol diacrylate, propylene glycol diacrylate, neopentyl glycol diacrylate, hexamethylene glycol diacrylate and bisphenol A diacrylate, 4,4'-bis(2-acryloyloxyethoxy) diphenylpropane, trimethylolpropane triacrylate, pentaerythritol triacrylate and pentaerythritol tetraacrylate, vinyl acrylate, divinylbenzene, divinyl succinate, diallyl phthalate, triallyl phosphate, triallyl isocyanurate and tris(2-acryloylethyl)isocyanurate.

Examples of higher molecular weight (oligomeric) polyunsaturated compounds are acrylated epoxy resins, acrylated or vinyl-ether- or epoxy-group-containing polyesters, polyurethanes and polyethers.

Further examples of unsaturated oligomers are unsaturated polyester resins, which are usually produced from maleic acid, phthalic acid and one or more diols and have molecular weights of about from 500 to 3000. In addition it is also possible to use vinyl ether monomers and oligomers, and also maleate-terminated oligomers having polyester, polyurethane, polyether, polyvinyl ether and epoxide main chains. Combinations of vinyl-ether-group-carrying oligomers and polymers, as described in U.S. Pat. No. 5,334,455, incorporated herein by reference, are especially suitable, but copolymers of monomers functionalised with vinyl ether and maleic acid also come into consideration.

Also suitable are compounds having one or more free-radical-polymerisable double bonds. The free-radical-polymerisable double bonds in such compounds are preferably in the form of (meth)acryloyl groups. Here and in the following, (meth)acryloyl and (meth)acrylic mean acryloyl and/or methacryloyl, and acrylic and/or methacrylic, respectively. At least two polymerisable double bonds in the form of (meth) acryloyl groups are preferably contained in the molecule. The compounds in question may be, for example, (meth)acryloyl-functional oligomeric and/or polymeric compounds of poly (meth)acrylate. The number-average molar mass of that compound may be, for example, from 300 to 10 000, preferably from 800 to 10 000, The compounds preferably containing free-radical-polymerisable double bonds in the form of (meth)acryloyl groups can be obtained by customary methods, for example by reaction of poly(meth)acrylates with (meth)acrylic acid. These and further preparation methods are described in the literature and known to the person skilled in the art.

Such unsaturated oligomers can also be termed prepolymers.

It is also possible to use in component (b) unsaturated acrylates having reactive functional groups. The reactive functional group may be selected, for example, from a hydroxy, thiol, isocyanate, epoxide, anhydride, carboxy, amino and blocked amino group. Examples of unsaturated acrylates containing OH groups are hydroxyethyl acrylates, hydroxybutyl acrylates and also glycidyl acrylates.

Examples of suitable monomers which are typically used to form the backbone (the base polymer) of such functionalised acrylate and methacrylate polymers are, for example, acrylate, methyl acrylate, methyl methacrylate, ethyl acrylate, ethyl methacrylate, n-butyl acrylate, n-butyl methacrylate, isobutyl acrylate, isobutyl methacrylate, 2-ethylhexyl acrylate, 2-ethylhexyl methacrylate, etc. In addition, suitable amounts of functional monomers are copolymerised during the polymerisation in order thus to obtain the functional polymers. Acid-functionalised acrylate or methacrylate polymers are obtained with the aid of acid-functional monomers such as acrylic acid and methacrylic acid. Hydroxy-functional acrylate or methacrylate polymers are obtained from hydroxy-functional monomers, such as 2-hydroxyethyl methacrylate, 2-hydroxypropyl methacrylate, 3,4-dihydroxybutyl methacrylate, or from acrylates which are derived from glycerol derivatives. Epoxy-functionalised acrylate or methacrylate polymers are obtained with the aid of epoxy-functional monomers such as glycidyl methacrylate, 2,3-epoxybutyl methacrylate, 3,4-epoxybutyl methacrylate, 2,3-epoxycyclohexyl methacrylate, 10,11-epoxyundecyl methacrylate, etc. Likewise, isocyanate-functionalised polymers, for example, can be produced from isocyanate-functionalised monomers, for example meta-isopropenyl-α,α-dimethylbenzyl isocyanate. Amino-functionalised polymers are, for example, polyacrylamides, and nitrile-group-containing polymers are, for example, polyacrylonitriles.

For example, typical of such compounds are ethylenically unsaturated mono- or polyfunctional carboxylic acids and polyols or polyepoxides, and polymers having ethylenically unsaturated groups in the chain or in side groups, e.g. unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and also mixtures of one or more such polymers.

Examples of suitable mono- or poly-functional unsaturated carboxylic acids are acrylic acid, methacrylic acid, crotonic acid, itaconic acid, cinnamic acid, maleic acid, fumaric acid, itaconic acid, and unsaturated fatty acids such as linolenic acid and oleic acid. Acrylic and methacrylic acid are preferred.

It is also possible to use saturated di- or poly-carboxylic acids in admixture with unsaturated carboxylic acids. Examples of suitable saturated di- or poly-carboxylic acids include, for example, tetrachlorophthalic acid, tetrabromophthalic acid, phthalic anhydride, adipic acid, tetrahydrophthalic acid, isophthalic acid, terepthalic acid, trimellitic acid, heptanedicarboxylic acid, sebacic acid, dodecanedicarboxylic acid, hexahydrophthalic acid, etc.

Suitable polyols include aromatic and, especially, aliphatic and cycloaliphatic polyols. Examples of aromatic polyols are hydroquinone, 4,4'-dihydroxydiphenyl, 2,2-di(4-hydroxyphenyl)propane, and novolaks and resols. Examples of polyepoxides are those based on the said polyols, especially the aromatic polyols and epichlorohydrin. Also suitable as polyols are polymers and copolymers that contain hydroxyl groups in the polymer chain or in side groups, e.g. polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols include alkylenediols having, for example, from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to be modified, for example etherified, or esterified by other carboxylic acids.

Specific examples of esters useful in component (b) include trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having a molecular weight of from 200 to 1500, and mixtures thereof.

The following esters are also suitable: dipropylene glycol diacrylate, tripropylene glycol diacrylate, 1,6-hexanediol diacrylate, glycerol ethoxylate triacrylate, glycerol propoxylate triacrylate, trimethylolpropane ethoxylate triacrylate, trimethylolpropane propoxylate triacrylate, pentaerythritol ethoxylate tetraacrylate, pentaerythritol propoxylate triacrylate, pentaerythritol propoxylate tetraacrylate, neopentyl glycol ethoxylate diacrylate, neopentyl glycol propoxylate diacrylate.

Also suitable as component (b) are the amides of identical or different unsaturated carboxylic acids and aromatic, cycloaliphatic and aliphatic polyamines having preferably from 2 to 6, especially from 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine and di(β-aminoethoxy)- and di(.beta.-aminopropoxy)-ethane. Further suitable polyamines are polymers and copolymers which may have additional amino groups in the side chain and oligoamides having amino terminal groups. Examples of such unsaturated amides are: methylene bisacrylamide, 1,6-hexamethylene bisacrylamide, diethylenetriamine trismethacrylamide, bis(methacrylamidopropoxy)ethane, β-methacrylamidoethyl methacrylate and N-[(β-hydroxyethoxy)ethyl]-acrylamide.

Suitable unsaturated polyesters and polyamides are derived, for example, from maleic acid and diols or diamines. The maleic acid may have been partially replaced by other dicarboxylic acids. They may be used together with ethylenically unsaturated comonomers, e.g. styrene. The polyesters and polyamides may also be derived from dicarboxylic acids and ethylenically unsaturated diols or diamines, especially from those having longer chains of e.g. from 6 to 20 carbon atoms. Examples of polyurethanes are those composed of saturated diisocyanates and unsaturated diols or unsaturated diisocyanates and saturated diols.

Aminoacrylates are also suitable for use in component (b). For example acrylates which have been modified by reaction with primary or secondary amines, as described, for example, in U.S. Pat. Nos. 3,844,916; 5,482,649; 5,734,002, each incorporated herein by reference, and EP 280 222. Such amine-modified acrylates are also termed aminoacrylates. Many suitable aminoacrylates are commercially available.

The photopolymerisable compounds (b) can be used alone or in any desired mixtures.

The photoinitiators of the instant invention are suitable quite generally as photoinitiators in a wide variety of systems in addition to coil coatings and metal primers, in particular, those systems comprising ethylenically unsaturated compounds. Such systems include, for example, overprint coatings, printing inks, systems used in the manufacture of electronic printed circuit boards and printing plates, and in the coating of various other substrates, such as wood, plastics, paper and glass The invention accordingly relates also to a composition comprising (b) at least one ethylenically unsaturated compound, for example, an acrylate or amino acrylate, (c) a photoinitiator of formula I, II or III, in particular the compounds identified as novel above, (d) optionally, further photoinitiators and co initiators (e) optionally a film-forming binder based on a thermoplastic or thermocurable resin; (f) optionally, further additives. Of course, each of the optional components (d), (e) and (f) may also be part of the coated metal surface of the instant invention.

Component (e) is, for example, generally a film-forming binder based on a thermoplastic or thermocurable resin, predominantly on a thermocurable resin. Examples thereof are alkyd, acrylic, polyester, phenol, melamine, epoxy and polyurethane resins and mixtures thereof. Examples thereof are described, for example, in Ullmann's Encyclopedia of Industrial Chemistry, 5th Ed., Vol. A18, pp. 368 426, VCH, Weinheim 1991.

Component (e) may be a cold-curable or hot-curable binder, with the addition of a curing catalyst possibly being advantageous. Suitable catalysts that accelerate the full cure of the binder are described, for example, in Ullmann's Encyclopedia of Industrial Chemistry, Vol. A18, page 469, VCH Verlagsgesellschaft, Weinheim 1991.

Examples of particular binders suitable as component (e) are: 1. surface-coating compositions based on cold- or hot-crosslinkable alkyd, acrylate, polyester, epoxy or melamine resins or mixtures of such resins, optionally with the addition of a curing catalyst; 2. two-component polyurethane surface-coating compositions based on hydroxyl-group-containing acrylate, polyester or polyether resins and aliphatic or aromatic isocyanates, isocyanurates or polyisocyanates; 3. two-component polyurethane surface-coating compositions based on thiol-group-containing acrylate, polyester or polyether resins and aliphatic or aromatic isocyanates, isocyanurates or polyisocyanates; 4. single-component polyurethane surface-coating compositions based on blocked isocyanates, isocyanurates or polyisocyanates, which are unblocked during stoving; the addition of melamine resins is also possible; 5. single-component polyurethane surface-coating compositions based on aliphatic or aromatic urethanes or polyurethanes and hydroxyl-group-containing acrylate, polyester or polyether resins; 6. single-component polyurethane surface-coating compositions based on aliphatic or aromatic urethane acrylates or polyurethane acrylates having free amine groups in the urethane structure, and melamine resins or polyether resins, optionally with the addition of a curing catalyst; 7. two-component surface-coating compositions based on (poly)ketimines and aliphatic or aromatic isocyanates, isocyanurates or polyisocyanates; 8. two-component surface-coating compositions based on (poly)ketimines and an unsaturated acrylate resin or a polyacetoacetate resin or a methacrylamidoglycolate methyl ester; 9. two-component surface-coating compositions based on carboxyl- or amino-group-containing polyacrylates and polyepoxides; 10. two-component surface-coating compositions based on anhydride-group-containing acrylate resins and a polyhydroxy or polyamino component; 11. two-component surface-coating compositions based on acrylate-containing anhydrides, and polyepoxides; 12. two-component surface-coating compositions based on (poly)oxazolines and anhydride-group-containing acrylate resins, or unsaturated acrylate resins or aliphatic or aromatic isocyanates, isocyanurates or polyisocyanates; 13. two-component surface-coating compositions based on unsaturated (poly)acrylates and (poly)malonates; 14. thermoplastic polyacrylate surface-coating compositions based on thermoplastic acrylate resins or extrinsically crosslinking acrylate resins, in combination with etherified melamine resins; 15. surface-coating composition systems, especially clear surface-coating compositions, based on malonate-blocked isocyanates with melamine resins (e.g. hexamethoxymethylG16 melamine) as crosslinker (acid-catalysed); 16. UV-curable systems based on oligomeric urethane acrylates and/or acylate acrylates, optionally with the addition of other oligomers or monomers; 17. dual-cure systems, which are first cured thermally and then UV-cured, or vice versa, constituents of the surface-coating composition containing double bonds which can be made to react by UV light and photoinitiators and/or by electron-beam curing.

In addition to the photoinitiator, the photopolymerisable mixtures may optionally comprise further conventional additives (f), depending on the intended use.

Examples thereof are: antioxidants, optical brighteners, fillers, thermal inhibitors which are intended to prevent premature polymerisation, antistats, wetting agents or flow improvers, further adhesion enhancers; thermal drying or curing catalysts, for example organometallic compounds, amines or/and phosphines; UV absorbers and light stabilizers, for example those from the group of the 2-(2'-hydroxyphenyl)-benzotriazoles, of the 2-hydroxybenzophenones, esters of unsubstituted or substituted benzoic acids, acrylates, sterically hindered amines, oxalic acid diamides, 2-(2-hydroxy-phenyl)-1,3,5-triazines, phosphites and phosphonites. Such compounds are common in the art and are also described in Published US appl. No. 20060270748, incorporated herein in its entirety by reference.

Photopolymerisation can also be accelerated by addition, as further additives (f), of photosensitisers that shift or broaden the spectral sensitivity. These include especially aromatic carbonyl compounds, for example benzophenone, thioxanthone, including especially isopropylthioxanthone, anthraquinone and 3-acylcoumarin derivatives, terphenyls, styryl ketones, and 3-(aroylmethylene)-thiazolines, camphorquinone and also eosin, rhodamine and erythrosine dyes.

The formulations may also comprise dyes and/or white or coloured pigments. Depending on the intended use, both inorganic and organic pigments may be used.

The additives (f) described above are conventional in the art and accordingly are used in the amounts customary in the art.

It is also possible to add solvents or water to the coating compositions herein. Suitable solvents are solvents which are known to the person skilled in the art and are conventional especially in coating technology. Radiation-curable aqueous prepolymer dispersions are obtainable commercially in many variations. They are to be understood as being a dispersion of water and at least one prepolymer dispersed therein.

The coating composition, for example, the coating layer of the coated metal surface may be a powder coating. The powder coatings may be based on solid resins and monomers containing reactive double bonds (compounds (b)), for example maleates, vinyl ethers, acrylates, acrylamides and mixtures thereof. The powder coatings may also comprise binders, as are described, for example, in U.S. Pat. No. 5,620,751, incorporated herein in its entirety by reference, and EP 636 669. The UV-curable powder coatings may also comprise white or coloured pigments.

It is also possible that the coating layer is a "dual cure" coating formulation using the photoinitiators according to the invention. Such formulations are known to the person skilled in the art and are both thermally cured and UV-cured. Such formulations can be found, for example, in U.S. Pat. No. 5,922,473, incorporated herein in its entirety by reference.

Frequently, the coating layer comprising components (b) and (c), and any additional optional components, is in the form of a dispersion. Dispersants useful in such an application are well known in the art, e.g., U.S. Pat. No. 7,084,183, incorporated herein in its entirety by reference.

A substrate, for example, a metal substrate, can be coated by applying a liquid composition, i.e., a solution or a suspension comprising components (b) and (c), plus any optional components, to the substrate. The choice of solvent and its concentration are governed chiefly by the nature of the composition and the coating method. The solvent is frequently inert, that is to say it does not enter into any chemical reaction with the components, although reactive diluents are known and may be used, and it should be capable of being removed again on drying after the coating operation. Suitable inert solvents include, for example, ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

The coating formulation is applied uniformly to a substrate by means of known coating methods, for example by spin-coating, immersion, knife coating, curtain pouring, brush application or spraying, especially by electrostatic spraying and reverse-roll coating, and also by electrophoretic deposition. It is also possible to apply the photosensitive layer to a temporary flexible support and then coat the final substrate by transferring the layer via lamination. Examples of types of application are to be found, for example, in Ullmann's Encyclopedia of Industrial Chemistry, 5th Edition, Vol. A18, pp. 491 500.

The amount applied (layer thickness) and the nature of the substrate (layer support) are dependent on the desired field of application. The range of dry layer thicknesses generally includes values from about 0.1 micron to more than about 100 microns.

The photosensitivity of the compositions according to the invention usually extends from approximately 200 nm to within the IR range, often UV light, about 200 nm to about 400 nm is very effective. Generally, light from about 200 nm to about 450 nm can be employed with excellent success. Suitable radiation is present, for example, in sunlight or light from artificial light sources. Accordingly a large number of the most varied kinds of light source may be used. Both point sources and planiform radiators (lamp carpets) are suitable. Examples are: carbon arc lamps, xenon arc lamps, medium-pressure, high-pressure and low-pressure mercury radiators, doped, where appropriate, with metal halides (metal halide lamps), microwave-excited metal vapour lamps, excimer lamps, superactinic fluorescent tubes, fluorescent lamps, argon incandescent lamps, flash lamps, e.g. high-energy flash lamps, photographic floodlight lamps, light-emitting diodes (LED), electron beams and X-rays. The distance between the lamp and the substrate to be exposed may vary according to the intended use and the type and strength of the lamp and may be, for example, from 2 cm to 150 cm. Laser light sources are suitable, for example excimer lasers, such as Krypton-F lasers for exposure at 248 nm. Lasers in the visible range may also be used.

As already mentioned, curing in the process according to the invention can be carried out simply by irradiation with electromagnetic radiation. Depending on the composition of the formulation to be cured, however, thermal curing before, during or after the irradiation is advantageous.

Thermal curing is carried out by methods known to the person skilled in the art. In general, the curing is carried out in an oven, e.g. a circulating air oven, on a hot plate or by irradiation with IR lamps. Unassisted curing at room temperature is also possible, depending on the binder system used. The curing temperatures are generally between room temperature and 150° C., for example from 25 to 150° C., or from 50 to 150° C. In the case of powder coatings or coil coatings, the curing temperatures may be even higher, e.g. up to 350° C.

One particular embodiment of the invention is a formulation useful as a primer coil coating which comprises a compound wherein an alpha hydroxy ketone photoinitiator moiety is chemically bound to an adhesion promoter such as a carboxylic acid, a phosphonate, or a trialkoxy silane. The coating formulation of the invention can of course be over-coating with one or more additional coating layers.

Measurement of physical properties of a UV cured primer over metal showed good to excellent adhesion of the primer layer obtained using the instant photoinitiators that are chemically bound to adhesion promoters. The instant photoinitiators, in some cases, gave primer layers with better adhesion properties than did photoinitiators that were not chemically modified with adhesion promoters.

EXAMPLES

Example 1A

2-Hydroxy-2-methyl-1-[4-(2-oxiranylmethoxy-ethoxy)phenyl]propan-1-one

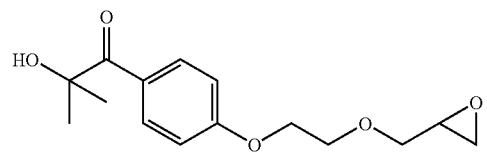 [SMILES: CC(C)(O)C(=O)c1ccc(OCCOCC2CO2)cc1]

Epichlorohydrin (24 g, 0.261 mol) is added to a mixture of 16.31 g (0.408 mol) of sodium hydroxide, 45 ml of water, and 0.761 g (2.24 mmol) of tetrabutylammonium hydrogen sulfate that is previously cooled in an ice-water bath for 20 minutes. To this mixture is added dropwise over 45 minutes with rapid stirring, a solution of 10.32 g (46.0 mmol) of 2-hydroxy-1-[4-(2-hydroxy-ethoxy)phenyl]-2-methylpropan-1-one in 95 ml of 1,2-dimethoxyethane. The reaction mixture is stirred overnight at room temperature. The aqueous layer is removed, and the organic layer is concentrated. Purification by flash chromatography on silica gel (1:1 heptane:ethyl acetate) affords 9.20 g (71% of theoretical yield) of the title compound, a pale yellow liquid.

Example 1B

Mixture of 2-Hydroxy-1-(4-{2-[2-hydroxy-3-(3-triethoxysilylpropylamino)propoxy]ethoxy}-phenyl)-2-methylpropan-1-one and 2-Hydroxy-1-[4-(2-{2-hydroxy-3-[(2-hydroxy-3-{2-[4-(2-hydroxy-2-methylpropionyl)phenoxy]ethoxy}propyl)-(3-triethoxysilylpropyl)amino]-propoxy}ethoxy)phenyl]-2-methylpropan-1-one

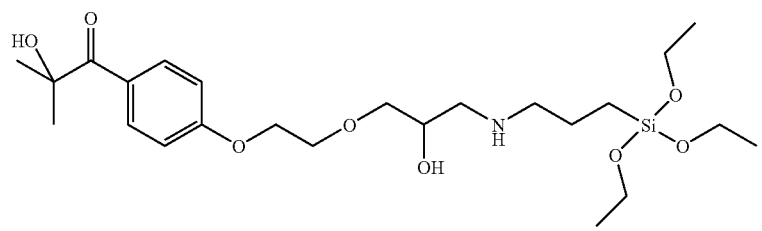

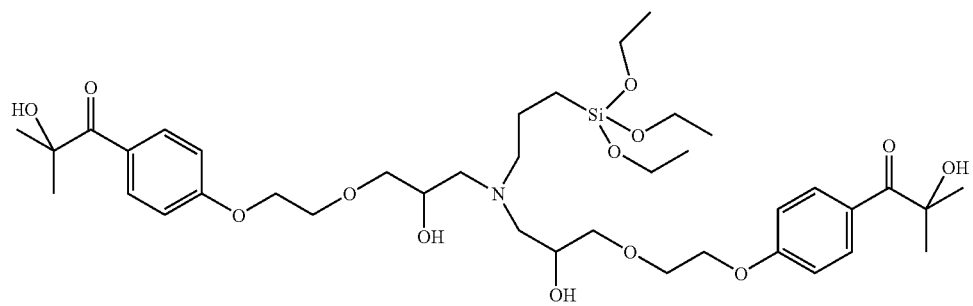

To a mixture of 5.09 g (23 mmol) of 3-aminopropyltriethoxysilane, 30 ml of 1,2-dimethoxyethane and 30 ml of 2-propanol is added 8.99 g (32.1 mmol) of the compound prepared in Example 1A. The reaction mixture is heated at a gentle reflux for 23 hours. Solvent is evaporated to afford 14.37 g of a pale yellow oil corresponding to a mixture of the title compounds.

Example 2

1-[4-(2-{3-[Bis(2-hydroxyethyl)amino]-2-hydroxypropoxyethoxy}phenyl]-2-hydroxy-2-methylpropan-1-one

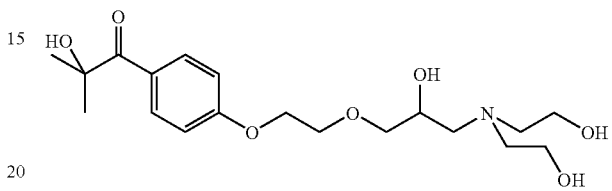

To a mixture of 3.23 g (30.7 mmol) of diethanolamine in 32 ml of 2-propanol is added a solution of 9.01 g (32.1 mmol) of the compound of Example 1A in 20 ml of 1,2-dimethoxyethane. The mixture is heated at reflux for 4 hours. An additional portion of diethanolamine (0.47 g, 4.47 mmol) is added to the reaction mixture, and the reaction is heated at reflux for 5 hours. Solvent is evaporated to obtain 13.37 g of the title compound, a yellow oil.

Example 3

Mixture of 2-Hydroxy-1-(4-{2-[2-hydroxy-3-(3-hydroxypropylamino)propoxy]ethoxy}-phenyl)-2-methylpropan-1-one and 2-Hydroxy-1-[4-(2-{2-hydroxy-3-[(2-hydroxy-3-{2-[4-(2-hydroxy-2-methylpropionyl)-phenoxy]ethoxy}propyl)-(3-hydroxypropyl)amino]-propoxy}ethoxy)phenyl]-2-methylpropan-1-one

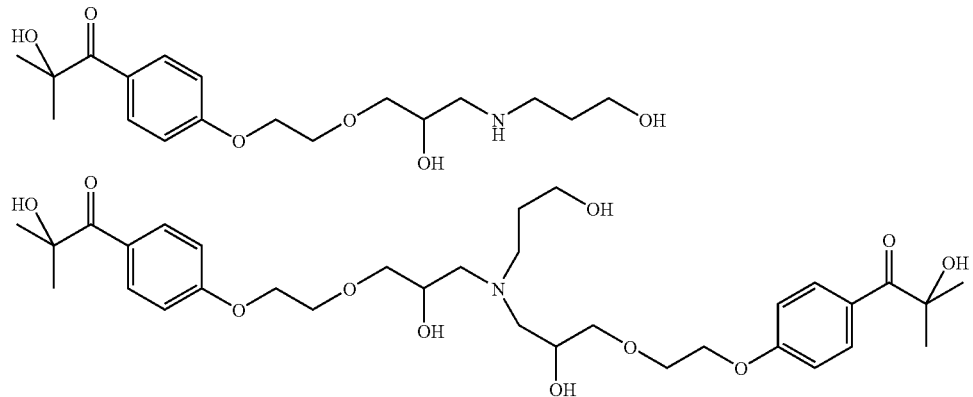

To a mixture of 2.22 g (29.6 mmol) of 3-amino-1-propanol in 20 ml of 1,2-dimethoxyethane and 40 ml of 2-propanol is added a solution of 11.57 g (41.3 mmol) of the compound of Example 1A in 20 ml of 1,2-dimethoxyethane. The mixture is heated at reflux overnight. Solvent is evaporated to afford a mixture of the title compounds.

Example 4

[4-(2-Hydroxy-2-methylpropionyl)phenoxy]acetic acid

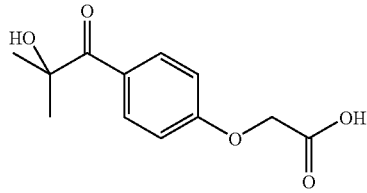 [SMILES: CC(C)(O)C(=O)c1ccc(OCC(=O)O)cc1]

A chilled mixture (0° C.) of acetonitrile (200 ml) and water (300 ml) is added drop wise to a chilled mixture of 15.0 g (66.9 mmol) of 2-hydroxy-1-[4-(2-hydroxyethoxy)phenyl-2-methylpropan-1-one, 2.00 g (9.38 mmol) of 1-oxyl-4-acetamido-2,2,6,6-tetramethylpiperidine, 4.00 g (12.4 mmol) of iodobenzene diacetate, and 5.0 g (59.5 mmol) of sodium bicarbonate. The reaction mixture is stirred 15 minutes at 0° C., and 5.1 g (61 mmol) of sodium bicarbonate is added. The reaction mixture is stirred for 2 hours at 0° C. The reaction is warmed to room temperature, and stirred for 90 minutes. The reaction mixture is made basic by the addition of sodium hydroxide, and then filtered. The filtrate is acidified and extracted with chloroform. The organic layer is concentrated to give 20 g of crude yellow oil that is crystallized to give 11 grams (69% yield) of the title compound, a tan solid.

Example 5

1-{2-[4-(2-hydroxy-2-methylpropionyl)phenoxy]ethyl}hydrogen 2-(3-triethoxysillylpropyl)succinate 1-{3-[4-(2-hydroxy-2-methylpropionyl)phenoxy]ethyl}hydrogen 2-(3-triethoxysillylpropyl)succinate

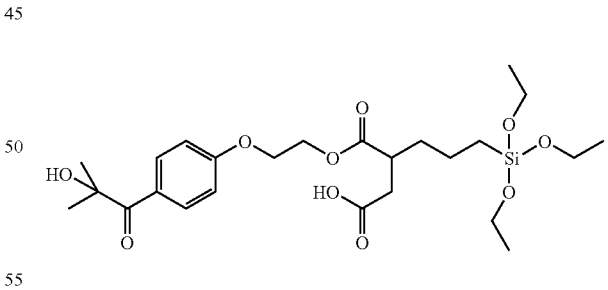

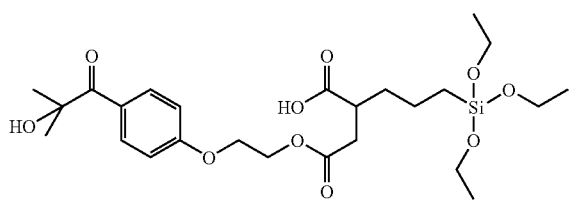

2-Hydroxy-1-[4-(2-hydroxyethoxy)phenyl-2-methylpropan-1-one (4.5g, 20.1 mmol), pyridine (2.13 g) and 1,2- dimethoxyethane (30 ml) are mixed together. After solids dissolve, 3-(triethoxysilyl)propylsuccinic anhydride (6.14 g, 20.2 mmol) is added and the mixture is allowed to stand at room temperature for one hour. The reaction mixture is then heated at 50° C. for 5 hours (oil bath). The mixture is cooled slowly and stirred overnight (16 hours) at room temperature.

The reaction solution is divided into two equal parts. Solvent is evaporated from one part to give 5.36 g of light brown viscous oil, which is a mixture of the title compounds.

The other half of the crude product mixture is stirred overnight with 8.3 g of Dowex 50W-2 100-200 mesh ion-exchange resin. The resin is removed by filtration, and solvent is evaporated to give 5.87 g of light brown oil, which is a mixture of the title compounds.

Example 6

3,3'-Bis[{2-[4-(2-hydroxy-2-methylpropionyl)phenoxy]ethoxy}carbonyl]benzophenone-4,4'-dicarboxylic acid 3,4'-Bis[{2-[4-(2-hydroxy-2-methylpropionyl)phenoxy]ethoxy}carbonyl]benzophenone-4,4'-dicarboxylic acid 4,4'-Bis[{2-[4-(2-hydroxy-2-methylpropionyl)phenoxy]ethoxy}carbonyl]benzophenone-4,4'-dicarboxylic acid

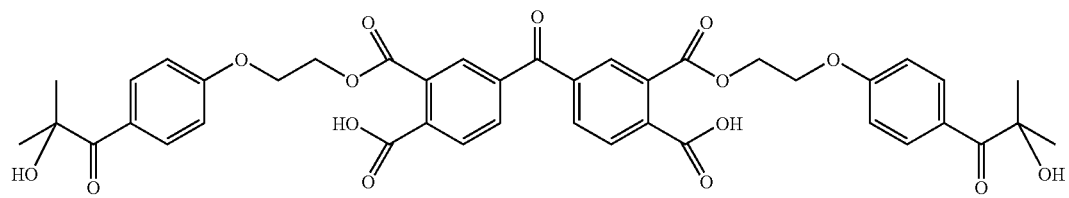

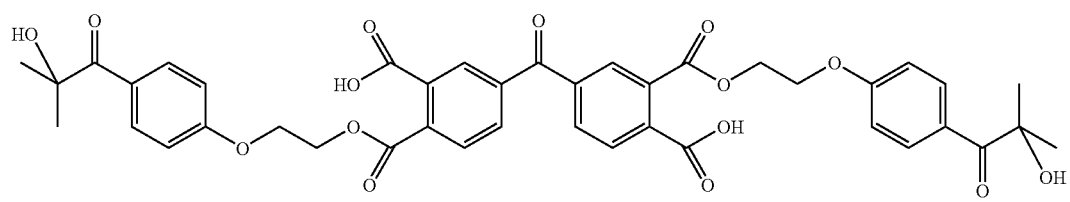

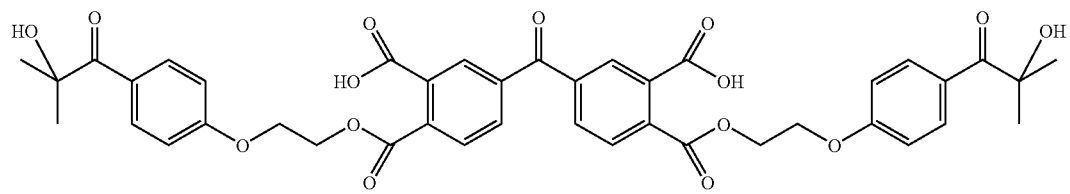

The reaction product, a mixture of isomers, is obtained by stirring 8.96 g (40.0 mmol) of 2-hydroxy-1-[4-(2-hydroxyethoxy)phenyl-2-methylpropan-1-one, 6.64 g (20.6 mmol) of 3,3',4,4'-benzophenonetetracarboxylic dianhydride and 1.75 g (22.1 mmol) of pyridine in 60 ml of tetrahydrofuran at 70° C. until the reaction is complete. Solvent is evaporated to obtain 14.56 g of light brown oil.

Example 7

4-{2-[4-(2-hydroxy-2-methylpropionyl)phenoxy]ethyl}hydrogen (Z)-2-Methylbut-2-enedioate 1-{2-[4-(2-hydroxy-2-methylpropionyl)phenoxy]ethyl}hydrogen (Z)-2-Methylbut-2-enedioate

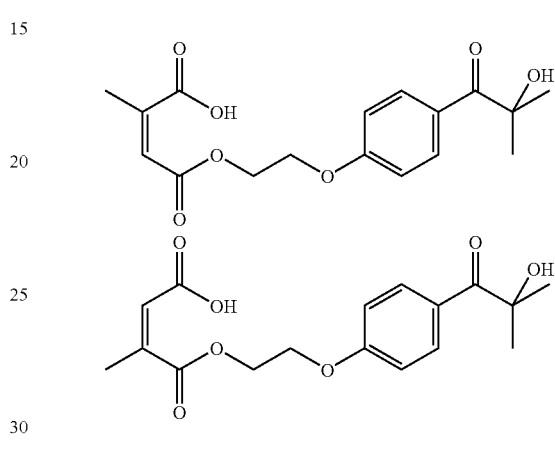

To a mixture of 6.72 g (0.0300 mol) of 2-hydroxy-1-[4-(2-hydroxyethoxy)phenyl-2-methylpropan-1-one and 3.49 g (0.0311 mol) of citraconic anhydride, dissolved in 50 ml of tetrahydrofuran, is added, at room temperature, 3 drops of pyridine. The reaction mixture is heated at 60° C. for 16 hours. Solvent is evaporated to give 10.24 g of an oil, which is a mixture of the title compounds.

Example 8

1-(2-Carboxy-3-hydroxy-2-methylpropyl)3,5-bis-{2-[4-(2-hydroxy-2-methylpropionyl)phenoxy]ethyl}benzene-1,3,5-tricarboxylate

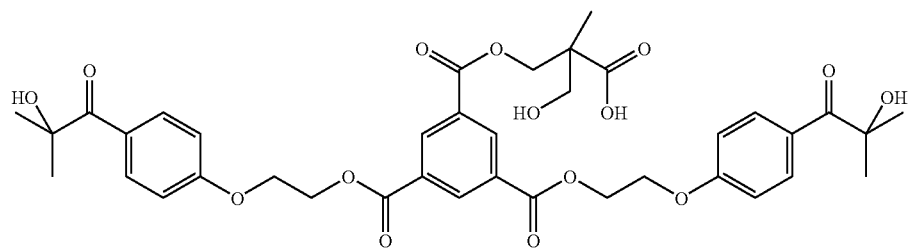 [SMILES: CC(C)(O)C(=O)c1ccc(OCCOC(=O)c2cc(C(=O)OCCOc3ccc(C(=O)C(C)(C)O)cc3)cc(C(=O)OCC(C)(CO)C(=O)O)c2)cc1]

A mixture of 6.72 g (30.0 mmol) of 2-hydroxy-1-[4-(2-hydroxyethoxy)phenyl-2-methylpropan-1-one and 50 ml of 1,2-dimethoxyethane is heated to 50° C. 1,3,5-Benzenetricarboxylic acid chloride (5.31 g, 20.0 mmol) is added, followed by 3.10 g (39.2 mmol) of pyridine. The mixture becomes cloudy. The reaction mixture is stirred overnight at 40° C., and the temperature is raised to 70° C. After 4 hours, 2,2-bis(hydroxymethyl) propionic acid (2.50 g, 18.6 mmol) is added to the reaction mixture, followed by 3.25 g (41.1 mmol) of pyridine. The reaction mixture is stirred overnight at 70° C. The reaction mixture is filtered and concentrated to obtain a light brown syrup which contains the title compound.

Example 9

2,4-Bis[{2-[4-(2-hydroxy-2-methyl-propionyl)phenoxy]ethoxy}carbonyl]benzene-1,5-dicarboxylic acid 1,4-Bis[{2-[4-(2-hydroxy-2-methyl-propionyl)phenoxy]ethoxy}carbonyl]benzene-1,5-dicarboxylic acid

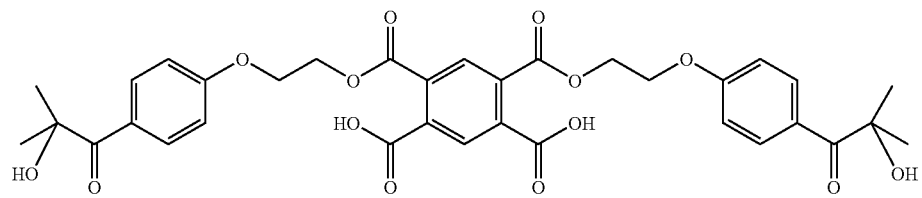

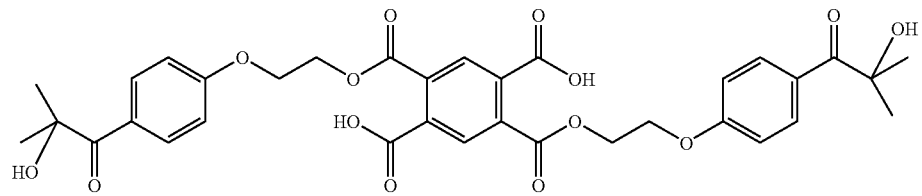

The reaction product mixture is obtained from benzene-1,2,4,5-tetracarboxylic anhydride, 2-hydroxy-1-[4-(2-hydroxyethoxy)phenyl-2-methylpropan-1-one and pyridine according to the procedure of Example 6.

Example 10

| 3,3'-Bis-{2-[4-(2-hydroxy-2-methylpropionyl)phenoxy]ethoxycarbonyl}biphenyl-4,4'-dicarboxylic acid | 5 |
| --- | --- |
| 3,4'-Bis-{2-[4-(2-hydroxy-2-methylpropionyl)phenoxy]ethoxycarbonyl}biphenyl-4,4'-dicarboxylic acid | 10 |

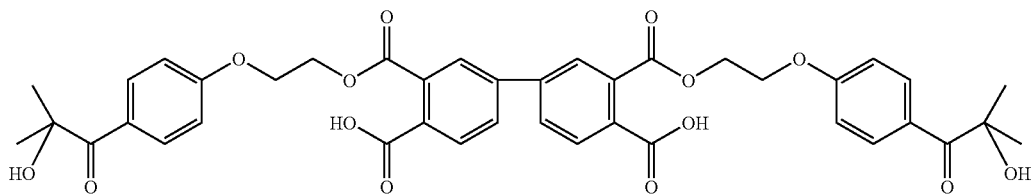

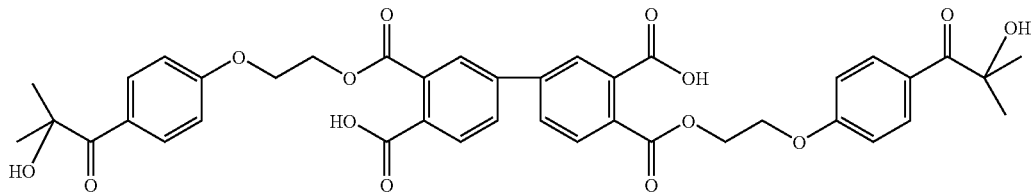

To 3,3'4,4'-biphenyltetracarboxylic dianhydride (3.00 g, 13.4 mmol) and 2-hydroxy-1-[4-(2-hydroxyethoxy)phenyl-2-methylpropan-1-one (4.49 g, 20.0 mmol) are added 40 ml dried, commercial tetrahydrofuran and pyridine (1.15 g, 14.5 mmol). The mixture is stirred at 70° C. until the reaction is complete. Most of the solvent is evaporated to give 11.0 g (contains solvent) of colorless, clear, viscous oily product, which is a mixture of isomers.

Example 11

Bis-[4-(2-hydroxy-2-methylpropionyl)phenyl]methyl (3-triethoxysilylpropyl)carbamate

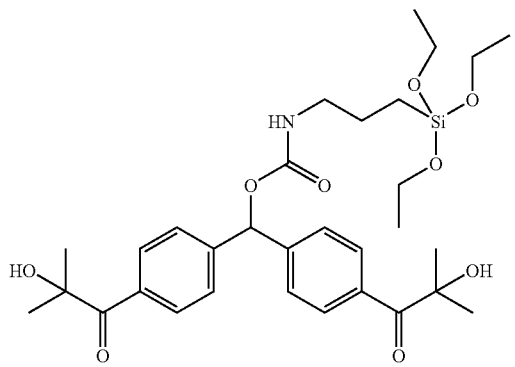 [SMILES: CCO[Si](CCCNC(=O)OC(c1ccc(C(=O)C(C)(C)O)cc1)c1ccc(C(=O)C(C)(C)O)cc1)(OCC)OCC]

A solution of 87.9 g (0.24 mol) of bis-[4-(2-hydroxy-2-methylpropionyl)phenyl]methanol in 1,2-dimethoxyethane is added to a mixture of 49.5 g (0.20 mol) of 3-triethoxysilylpropyl isocyanate and 0.097 g (0.20 mmol) of zirconium(IV) acetylacetonate. The reaction mixture is stirred at 60° until the reaction is complete. Solvent is evaporated to give the title compound.

Example 12

2-{3-[Bis-(2-hydroxyethyl)amino]-2-hydroxy-propoxy}-1-[4-(2-{3-[bis-(2-hydroxyethyl)amino]-2-hydroxy-propoxy}ethoxy)phenyl]-2-methylpropan-1-one

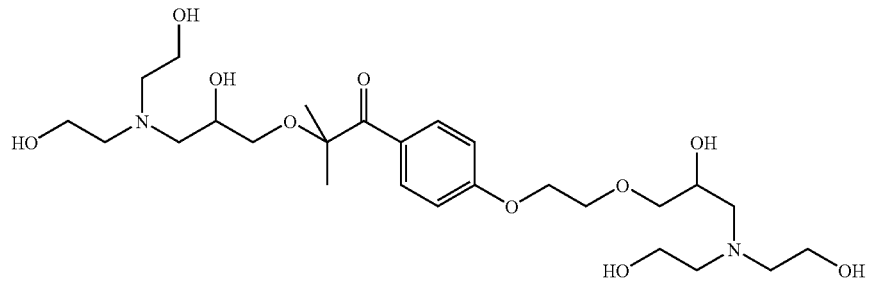 [SMILES: CC(C)(OCC(O)CN(CCO)CCO)C(=O)c1ccc(OCCOCC(O)CN(CCO)CCO)cc1]

The reaction time in Example 1A is extended. The aqueous layer is removed, and the organic layer is concentrated. Purification by flash chromatography on silica gel (1:1 heptane: ethyl acetate) affords 2-methyl-2-oxiranylmethoxy-1-[4-(2-oxiranylmethoxy-ethoxy)-phenyl]-propan-1-one. This compound is dissolved in 1,2-dimethoxyethane and the solution is added to a mixture of 1.8 equivalents of diethanolamine and isopropyl alcohol. The reaction mixture is heated overnight at reflux temperature. Solvent is evaporated to give a mixture of the title compound and the product of Example 2.

Example 13

3-{2-[4-(2-hydroxy-2-methylpropionyl)phenoxy] ethoxycarbonyl}benzophenone-3',4,4'-tricarboxylic acid 4-{2-[4-(2-hydroxy-2-methylpropionyl)phenoxy] ethoxycarbonyl}benzophenone-3',4,4'-tricarboxylic acid

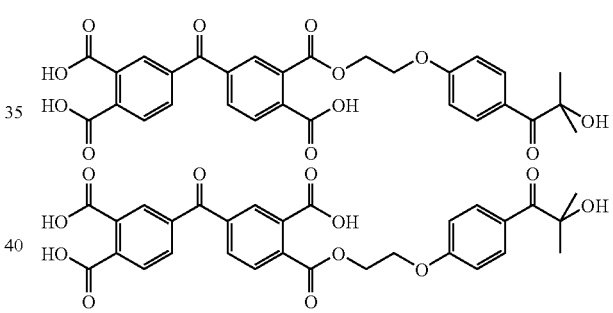

The reaction product, a mixture of isomers, is obtained by stirring 4.48 g (20.0 mmol) of 2-hydroxy-1-[4-(2-hydroxy-ethoxy)phenyl-2-methylpropan-1-one, 6.44 g (20.0 mol) of 3,3',4,4'-benzophenonetetracarboxylic dianhydride and 60 ml of 1,2-dimethoxyethane at 85° C. overnight. Solvent is evaporated to give 15.29 g of a semi-solid. Analysis (MS)

shows the majority of the material is consistent with the title compounds. The product also contains the product of Example 6.

Example 14

1-{2-[4-(2-hydroxy-2-methyl-propionyl)phenethyl}hydrogen2-(3-triethoxysillylpropyl)succinate 4-{2-[4-(2-hydroxy-2-methyl-propionyl)phenethyl}hydrogen 2-(3-triethoxysillylpropyl)succinate

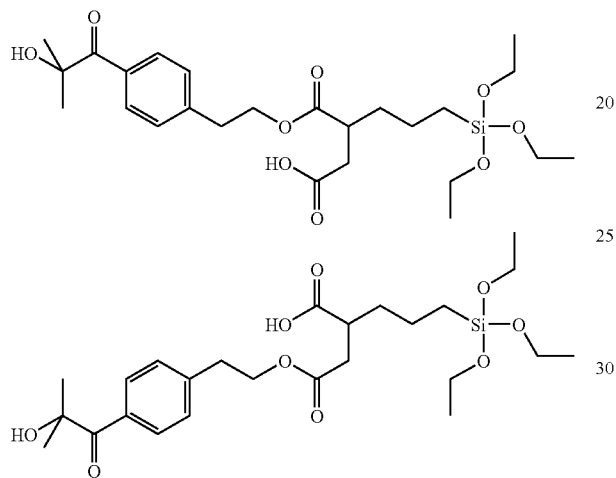

3-(Triethoxysilyl)propylsuccinic anhydride (6.32 g, 20.8 mmol) is added drop wise at room temperature to a mixture of 4.24 g (20.4 mmol) of 2-hydroxy-1-[4-(2-hydroxyethyl)phenyl-2-methylpropan-1-one (see Example 15), 1.65 g (20.9 mmol) of pyridine, and 30 ml of 1,2-dimethoxyethane. The reaction mixture is stirred at room temperature for 30 minutes, then at 50° C. until the reaction is complete. Most of the solvent is evaporated to obtain 14.06 g of an oil, which is a mixture of the title compounds.

Example 15

3,3'-Bis[{2-[4-(2-hydroxy-2-methylpropionyl)phenyl]ethoxy}carbonyl]benzophenone-4,4'-dicarboxylic acid 3,4'-Bis[{2-[4-(2-hydroxy-2-methylpropionyl)phenyl]ethoxy}carbonyl]benzophenone-4,4'-dicarboxylic acid

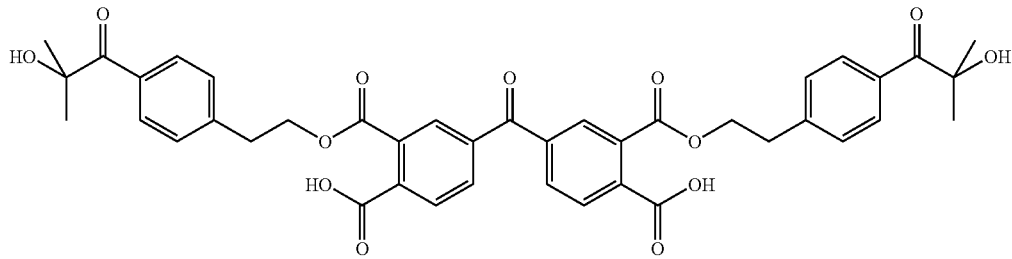

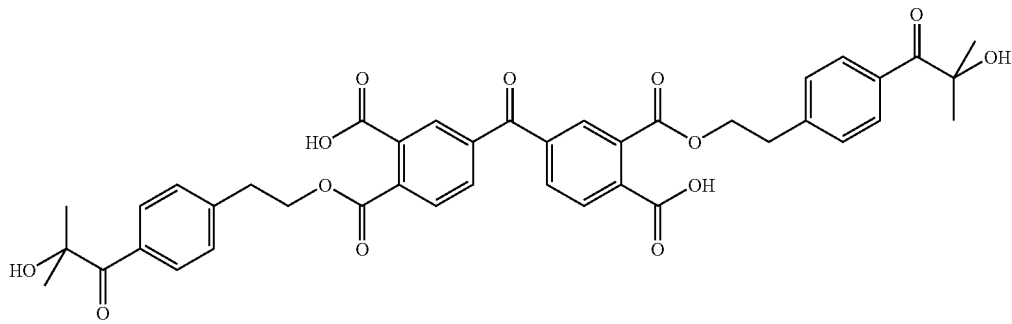

Isobutyryl chloride (114 g, 1.07 mol) is added drop wise at −5 to 0° C. over 40 minutes to 295 g (2.21 mol) of anhydrous aluminum chloride in 160 ml of methylene chloride. Stirring is continued for 30 min, and 2-phenylethyl acetate (164.2 g, 1.00 mol) is then added drop wise at −5 to 0° C. over 2 hours. The mixture is stirred an additional 4 hours at −5 to 0° C., and then poured into a mixture of concentrated hydrochloric acid and ice. The organic layer is washed with water, dried and concentrated to give 190.5 g of crude 2-(4-isobutyrylphenyl) ethyl acetate, a colorless liquid.

A 110 g portion of crude 2-(4-isobutyrylphenyl)ethyl acetate is dissolved in 100 ml of glacial acetic acid. Bromine (93.64 g, 0.59 mol) is added over one hour at 25° C. The mixture is stirred overnight at room temperature, and then poured into 1500 ml of water. The product is extracted with ethyl acetate. The combined extracts are dried and concentrated to give 160.11 g of 2-[4-(2-bromo-2-methyl-propionyl) phenyl]acetate, a viscous oil, which is dissolved in 200 ml of ethanol. A 32% sodium hydroxide solution is added over 20 minutes. The mixture is stirred until hydrolysis is complete, and ethanol is evaporated. The oily residue is poured into ice water, and this mixture is extracted with ethyl acetate. The organic layer is dried, filtered, and concentrated. One-half of the crude product is recrystallized from a mixture of acetone and petroleum ether to give 12.78 g of 2-hydroxy-1-[4-(2-hydroxyethyl)phenyl]-2-methylpropan-1-one, a white crystalline solid.

Pyridine (2.43 g, 30.7 mmol) is added to a mixture of 6.24 g (30.0 mmol) of 1-[4-(2-hydroxyethyl)phenyl]-2-hydroxy-2-methylpropan-1-one, 4.83 g (15.0 mmol) of benzophenone-3,3',4,4'-tetracarboxylic dianhydride, and 80 ml ethylene glycol dimethyl ether. The mixture is stirred at 80° C. for 12 hours. Solvent is evaporated to give 15 g of light brown viscous oil, a mixture of the title compounds.

Example 16

1-{3,3-Bis-[4-(2-hydroxy-2-methylpropionyl)phenyl]propyl}succinate

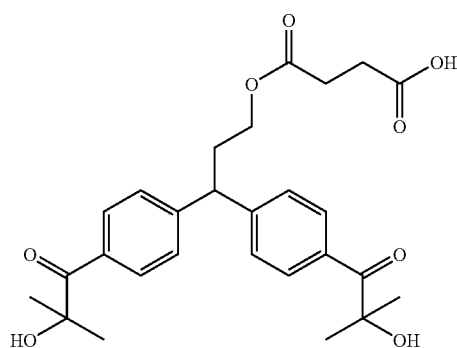 [SMILES: CC(C)(O)C(=O)c1ccc(C(CCOC(=O)CCC(=O)O)c2ccc(C(=O)C(C)(C)O)cc2)cc1]

{3,3-Bis-[4-(2-hydroxy-2-methylpropionyl)phenyl]propanol is prepared from 3,3-diphenylpropyl acetate by Friedel-Crafts acylation, bromination, and hydrolysis according to the method of Example 27. The alcohol is dissolved in 1,2-dimethoxyethane and reacted with succinic anhydride and pyridine according to the method of Example 10 to give the title compound.

Example 17

Methyl 3-[(2-{2-[4-(2-Hydroxy-2-methylpropionyl) phenoxy]ethoxycarbonyl}ethyl)(3-[(2-{2-[4-(2-hydroxy-2-methylpropionyl)phenoxy]ethoxydimethoxysilylpropyl)]amino]propionate

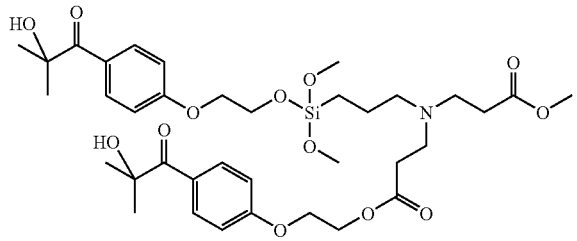 [SMILES: COC(=O)CCN(CCC[Si](OC)(OC)OCCOc1ccc(C(=O)C(C)(C)O)cc1)CCC(=O)OCCOc1ccc(C(=O)C(C)(C)O)cc1]

3-Aminopropyltrimethoxysilane (11.05 g, 61.7 mmol) and methanol (20 ml) are stirred together for 30 minutes at room temperature. To the mixture is added 41.46 g (482 mmol) of methyl acrylate. The reaction mixture is heated overnight in a 30° C. oil bath. The reaction mixture is concentrated at reduced pressure to give 21.50 g of crude methyl 3-[(2-methoxycarbonylethyl)-(3-trimethoxysilylpropyl)amino]propionate, a yellow viscous oil. A mixture of the crude product, 1-[4-(2-hydroxyethyoxy)phenyl]-2-hydroxy-2-methylpropan-1-one (26.85 g, 119.7 mmol) and 1,2-dimethoxyethane (80 ml) is heated in an oil bath at 85° (bath temperature). Zirconium(IV) acetylacetonate (1.16 g, 2.38 mmol) is added, and the mixture is stirred at 85° C. overnight and then at room temperature for 24 hours. Solvent is evaporated, and approximately one-half of the crude product is passed through a silica gel column with 5:1 chloroform:methanol as eluent to obtain 15.74 g of the title compound, a yellow semisolid product.

Example 18

Methyl3-[(2-{2-[4-(2-Hydroxy-2-methylpropionyl) phenoxy]ethoxycarbonyl}ethyl)(3-[(2-{2-[4-(2-hydroxy-2-methylpropionyl)phenoxy]ethoxydiethoxysilylpropyl)]amino]propionate

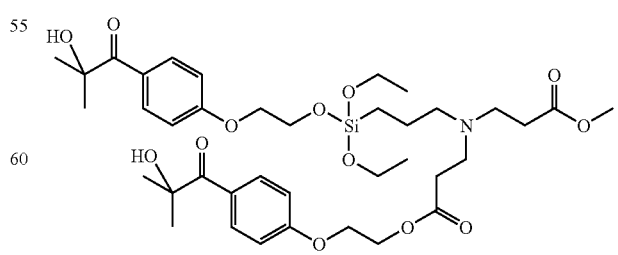

The procedure of Example 17 is repeated using 3-aminotriethoxysilane to obtain the title compound.

Example 19

5-[Bis-(3-trimethoxysilylpropyl)carbamoyl]-1-{2-[4-(2-hydroxy-2-methylpropionyl)phenoxy]ethyl}ester3-{2-[4-(2-hydroxy-2-methylpropionyl)phenoxy]ethyl}1,3,5-benzenetricarboxylate

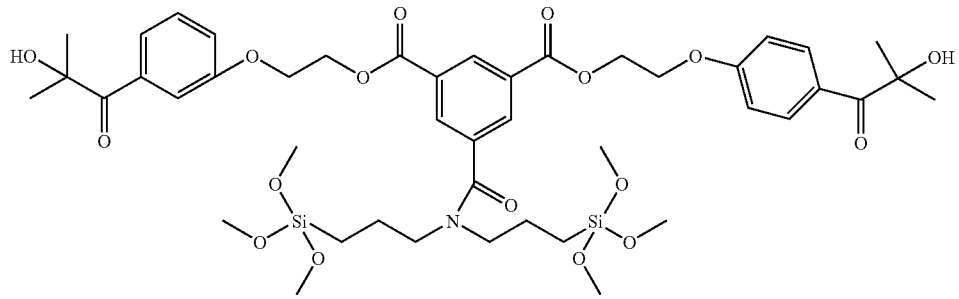 [SMILES: CO[Si](CCCN(CCC[Si](OC)(OC)OC)C(=O)c1cc(C(=O)OCCOc2ccc(C(=O)C(C)(C)O)cc2)cc(C(=O)OCCOc2cccc(C(=O)C(C)(C)O)c2)c1)(OC)OC]

To a solution of 4.10 g (15.4 mmol) of 1,3,5-benzenetricarrboxylic acid chloride in 50 of 1,2-dimethoxyethane is added 6.72 g (30.0 mmol) of 1-[4-(2-hydroxyethyoxy)phenyl]-2-hydroxy-2-methylpropan-1-one. A short time later, 3.76 g (47.5 mmol) of pyridine is added to the reaction mixture. The reaction is monitored by IR spectroscopy. The reaction mixture is stirred at room temperature for 40 minutes. To two-thirds of the reaction mixture is added drop wise 5.41 g (15.8 mmol) of bis(trimethoxysilylpropyl)amine. The reaction mixture is stirred for 20 minutes, filtered, and concentrated to give 12.32 g of yellow oil. The title compound is a major component of the reaction product.

Example 20

5-[(3-trimethoxysilylpropyl)carbamoyl]-1-{2-[4-(2-hydroxy-2-methylpropionyl)phenoxy]ethyl}ester3-{2-[4-(2-hydroxy-2-methylpropionyl)phenoxy]ethyl}1,3,5-benzenetricarboxylate

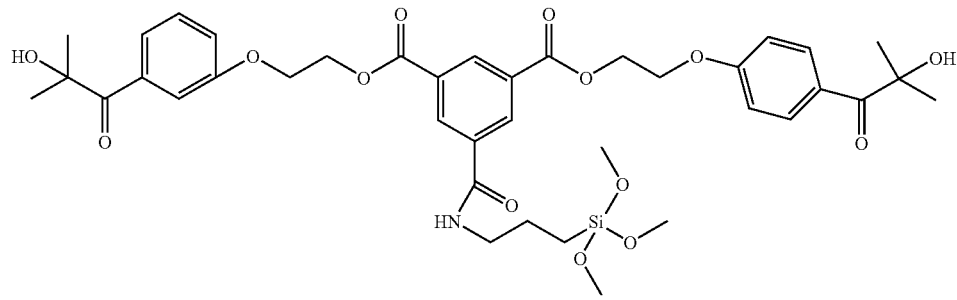 [SMILES: CO[Si](CCCNC(=O)c1cc(C(=O)OCCOc2ccc(C(=O)C(C)(C)O)cc2)cc(C(=O)OCCOc2cccc(C(=O)C(C)(C)O)c2)c1)(OC)OC]

Pyridine (3.72 g, 47.0 mmol) is added to a solution of 6.28 g (28.0 mmol) of 1-[4-(2-hydroxyethyoxy)phenyl]-2-hydroxy-2-methylpropan-1-one, 2.51 g (14.0 mmol) of 3-aminopropyltrimethoxysilane and 25 ml of tetrahydrofuran. The temperature is raised to 60° C., and a solution of 3.72 g (14.0 mmol) of 1,3,5-benzenetricarboxylic acid chloride in 20 ml of tetrahydrofuran is added to the reaction mixture drop wise over 10 minutes. The reaction mixture is stirred at 60° C. for 30 minutes, cooled to room temperature and filtered. Solvent is evaporated to obtain 11.95 g of an oil containing the title compound.

Example 21

2-[4-(2-hydroxy-2-methylpropionyl)phenoxy]ethyl (3-triethoxysilylpropyl)carbamate A mixture of 5.89 g (26.3 mmol) of 1-[4-(2-hydroxyethyoxy)phenyl]-2-hydroxy-2-methylpropan-1-one, 5.40 g (21.8 mmol) of 3-triethoxysilylpropyl isocyanate and 0.012 g (0.025 mmol) of zirconium(IV) acetonylacetonate in 50 ml of 1,2-dimethoxyethane is stirred at room temperature and then 60° C. until reaction is complete. Solvent is evaporated to give 11.32 g of product, a pale orange oil.

Example 22

{2-[4-(2-Hydroxy-2-methylpropionyl)phenoxyethyl}phosphonic acid

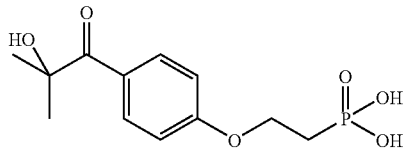 [SMILES: CC(C)(O)C(=O)c1ccc(OCCP(=O)(O)O)cc1]

A solution of trimethylsilyl bromide (8.7 g, 0.057 moles) in 25 ml of dichloromethane is added drop wise at room temperature to a mixture of 9.00 g (0.0285 mol) of {2-[4-(2-hydroxy-2-methylpropionyl)phenoxy]ethyl}phosphonic acid dimethyl ester (Example 23) and 75 ml of dichloromethane. The reaction mixture is stirred 5 hours at 25° C. Solvent is evaporated. Methanol (200 ml) is added, and the reaction mixture is stirred at room temperature for 24 hours. Solvent is evaporated to give 8 g of the title compound, a yellow oil.

Example 23

{2-[4-(2-Hydroxy-2-methylpropionyl)phenoxy]ethyl}phosphonic acid dimethyl ester

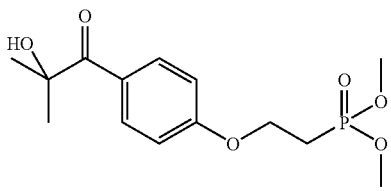 [SMILES: COP(=O)(CCOc1ccc(C(=O)C(C)(C)O)cc1)OC]

A solution of 43 g (0.128 mol) of carbon tetrabromide in 50 ml of dichloromethane is slowly added drop wise to a mixture of 14 g (0.062 mol) of 2-hydroxy-1-[4-(2-hydroxyethoxy) phenyl-2-methylpropan-1-one, 33 g (0.128 mol) of triphenyl phosphine and 150 ml of dichloromethane. The reaction is stirred overnight at room temperature. Solvent is evaporated, and the resulting oil is purified by flash chromatography on silica gel (8:2 heptane:ethyl acetate) to give 13 g (70% yield) of 1-[4-(2-bromoethoxy)phenyl]-2-hydroxy-2-methylpropan-1-one, a yellow solid.

A mixture of 5.80 grams (0.0202 mol) of 1-[4-(2-bromoethoxy)phenyl]-2-hydroxy-2-methylpropan-1-one and 6.27 g (0.0505 mol) of trimethyl phosphite is heated to 130° C. for 16 hours. The crude product is passed through a short column of silica gel which is eluted with a mixture of 1:1 heptane: ethyl acetate followed by methanol. Evaporation of solvent gives 3.5 g (55% yield) of the title compound as a yellow oil.

Example 24

2-Hydroxy-2-methyl-1-{4-[2-(2,4,8,10-tetra-tert-butyl-12H-dibenzo[d,g][1,3,2]dioxaphosphocin-6-yloxy)ethoxy]phenyl}propan-1-one

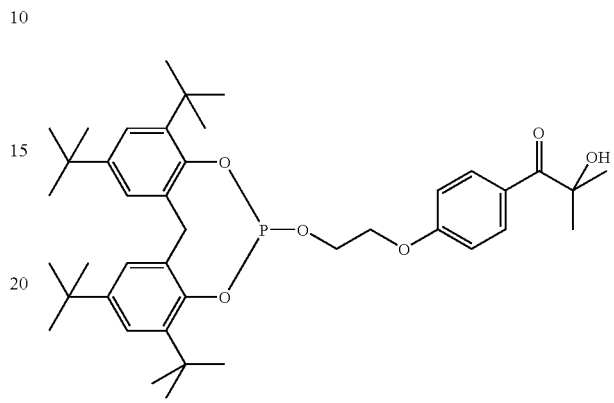

A mixture of 5.00 g (0.0223 moles) of 2,4,8,10-tetra-tert-butyl-6-chloro-12H-dibenzo[d,g][1,3,2]dioxaphosphocin, 11.0 g (0.0225 moles) of 2-hydroxy-1-[4-(2-hydroxyethoxy) phenyl]-2-methylpropan-1-one and 2.7 grams of triethylamine in 150 ml of dichloromethane is stirred at room temperature for 24 hours. The solvent is evaporated, and the crude material is recrystallized from a mixture of 95:5 acetonitrile: toluene to afford 9.5 g (63% yield) of a light pink solid.

Example 25

{2-[4-(2-Hydroxy-2-methylpropionyl)phenyl]ethyl}phosphonic acid

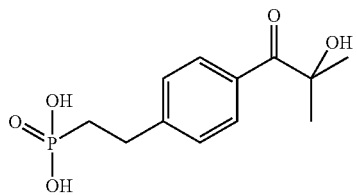 [SMILES: CC(C)(O)C(=O)c1ccc(CCP(=O)(O)O)cc1]

2-Bromoethylbenzene (10.0 g, 0.0540 mol) is mixed with 6.6 g (0.062 mol) of isobutyryl chloride and 100 ml of 1,2-dichlorobenzene. The mixture is cooled internally to 0° C., and 9.4 g (0.070 mol) of aluminum chloride is added portion wise over 3 hours while keeping the reaction mixture at 0-5° C. The reaction mixture is stirred overnight, then poured into a mixture of ice and concentrated hydrochloric acid. After stirring for 30 minutes, the organic layer is washed with dilute hydrochloric acid, sodium bicarbonate solution, and water, then dried over sodium sulfate and concentrated to give 15.0 g of crude 1-[4-(2-bromoethyl)phenyl]-2-methylpropan-1-one.

A solution of 10 g of bromine in 25 ml of 1,2-dichlorobenzene is added drop wise at room temperature to 13.0 g (0.0509 mol) of crude 1-[4-(2-bromoethyl)phenyl]-2-methylpropan-1-one that is dissolved in 100 ml of 1,2-dichlorobenzene. The reaction mixture is stirred overnight, and then poured into a 5% sodium thiosulfate solution. The mixture is stirred for 30 minutes, and the organic layer is washed with 5% sodium thiosulfate solution, sodium bicarbonate solution, and distilled water. The organic layer is passed through a pad of silica gel and eluted with 9:1 heptane:ethyl acetate to give, after concentration, 7.5 g (55% yield) of 2-bromo-1-[4-(2-bromoethyl)phenyl]-2-methylpropan-1-one.

A mixture of 5.0 g, 0.105 mol) of 2-bromo-1-[4-(2-bromoethyl)-phenyl]-2-methyl-propan-1-one, 0.60 g (0.015 mol) of sodium hydroxide, 100 ml of ethanol and 50 ml of 1,2-dimethoxyethane is stirred at room temperature overnight. The reaction mixture is concentrated and the crude product is dissolved in ethyl acetate. The solution is washed with distilled water, dried over sodium sulfate and concentrated to give 3.4 g of 1-[4-(2-bromoethyl)phenyl]-2-hydroxy-2-methylpropan-1-one.

A mixture of 10 g of 1-[4-(2-bromoethyl)phenyl]-2-hydroxy-2-methylpropan-1-one (0.037 moles) and 6.7 g (0.041 mol) of triethyl phosphite is heated externally at 140° C. for 24 hours. The reaction mixture is distilled to give 12.1 g of 2-[4-(2-hydroxy-2-methylpropionyl)phenyl] ethyl}phosphonic acid dimethyl ester. The ester is dissolved in 50 ml of dichloromethane, and a solution of 6.2 g (0.0405 mol) of trimethylsilyl bromide in 10 ml of dichloromethane is added drop wise at room temperature. The reaction mixture is stirred overnight. The reaction mixture is concentrated, and methanol (200 ml) is added. The mixture is stirred at temperature for 24 hours, and then concentrated to give 5.0 g of the title compound, a yellow oil.

Example 26

{3,3-Bis-[4-(2-hydroxy-2-methylpropionyl)phenyl]propyl}phosphonic acid

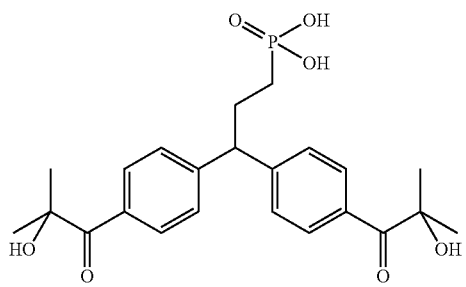 [SMILES: CC(C)(O)C(=O)c1ccc(C(CCP(=O)(O)O)c2ccc(C(=O)C(C)(C)O)cc2)cc1]

3,3-Diphenyl-1-bromopropanol (45 g, 99% yield) is prepared from the reaction of 35 g (0.164 mol) of 3,3-diphenyl-1-propanol, 71 g (0.214 mol) of carbon tetrabromide and 56 g (0.214 mol) of triphenylphosphine following the procedure of Example 23. The bromide is reacted with 38.4 g (0.359 mol) of isobutyryl chloride and 54.4 g (0.408 mol) of aluminum chloride according to the procedure of Example 25 to give 12.8 g (19% yield) of 1-{4-[3-bromo-1-(4-isobutyrylphenyl)propyl]phenyl}-2-methylpropan-1-one. This product is then reacted with bromine followed by sodium hydroxide and a catalytic amount of tetrabutylammonium bromide, according to the procedure of Example 25, to give 5.0 g of 1-(4-{3-bromo-1-[4-(2-hydroxy-2-methylpropionyl)phenyl]propyl}phenyl)-2-hydroxy-2-methylpropan-1-one.

1-(4-{3-Bromo-1-[4-(2-hydroxy-2-methylpropionyl)phenyl]propyl}phenyl)-2-hydroxy-2-methylpropan-1-one (5.0 g, 0.0112 moles) is reacted with 4.6 grams of triethyl phosphite following the procedure of Example 23 to give 5.7 g (98% yield) of {3,3-bis-[4-(2-hydroxy-2-methylpropionyl)phenyl]propyl}phosphonic acid dimethyl ester, a yellow oil. The ester is reacted with trimethylsilyl bromide in chloroform and methanol, following the procedure of Example 22, to give 5.0 g of the title compound, an amorphous solid.

Example 27

3-[4-(2-Hydroxy-2-methylpropionyl)phenyl]-3-phenylpropanoic acid

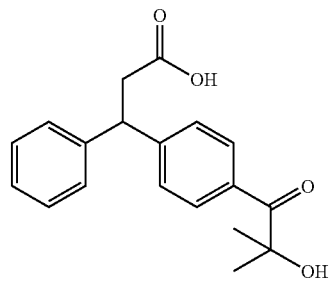 [SMILES: CC(C)(O)C(=O)c1ccc(C(CC(=O)O)c2ccccc2)cc1]

A mixture of 80 g (0.333 mol) of methyl 3,3-diphenylpropanoate, 42.6 g (0.399 mol) of isobutyryl chloride, and 600 mol of 1,2-dichlorobenzene is cooled to 4° C. Aluminum chloride (112 g, 0.832 mol) is added portion wise over 2 hours while the reaction temperature is kept between −5 and 5° C. The reaction is kept within this temperature range for 7 hours, and then stirred at room temperature for 13 hours. The reaction mixture is poured into a mixture of ice and concentrated hydrochloric acid, and then stirred for 1 hour. The organic layer is washed twice with dilute hydrochloric acid, and then concentrated under vacuum to give 115 grams of crude product. Purification by column chromatography on silica gel with 9:1 heptane:ethyl acetate as the eluent gives 69 g (60% yield) of methyl 3-[4-(2-methylpropionyl)phenyl]-3-phenylpropanoate.

A solution of 29.4 g (0.184 mol) of bromine in 50 ml of methylene chloride is added drop wise at room temperature to a mixture of 52.0 g (0.168 mol) of methyl 3-[4-(2-methylpropionyl)phenyl]-3-phenylpropanoate in 250 ml of methylene chloride. A small exotherm is controlled using a water bath.

The mixture is stirred for 16 hours at room temperature. The reaction mixture is poured into a 5% aqueous sodium thiosulfate solution and stirred for 10 minutes. The organic layer is washed twice with 5% aqueous sodium thiosulfate solution, once with 10% sodium bicarbonate solution, dried over sodium sulfate, and concentrated to give 64.0 grams (98% yield) of methyl 3-[4-(2-bromo-2-methylpropionyl)phenyl]-3-phenylpropanoate.

A mixture of 64.0 g (0.164 mol) of 3-[4-(2-bromo-2-methylpropionyl)phenyl]-3-phenylpropanoate, 13.2 g (0.328 mol) of sodium hydroxide, 70 ml of water, and 300 ml of 1,2-dimethoxyethane is heated at reflux for 16 hours. The reaction is concentrated, and then acidified with 25 ml of 1.5 N hydrochloric acid solution. Ethyl acetate (200 ml) is added, and the organic layer is washed with distilled water, dried over sodium sulfate, and concentrated. The crude product is passed through a pad of silica gel with ethyl acetate as the eluent to give 44 g (86% yield) of the title compound.

Example 28

1-[4-(2-{3-[Bis-(2-hydroxyethyl)amino]-2-hydroxypropoxy}ethyl)phenyl]-2-hydroxy-2-methylpropan-1-one

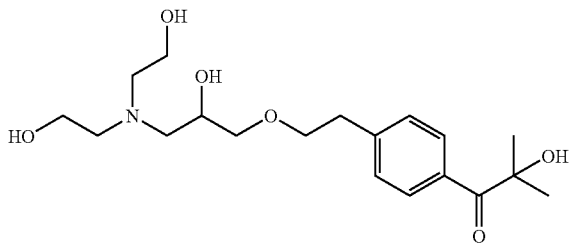 [SMILES: CC(C)(O)C(=O)c1ccc(CCOCC(O)CN(CCO)CCO)cc1]

The epoxide of 2-hydroxy-1-[4-(2-hydroxyethyl)phenyl]-2-methylpropan-1-one (see Example 15) is prepared according to the procedure of Example 1A. The epoxide is reacted with diethanolamine according to the procedure of Example 2 to give the title compound.

Example 29

2-Hydroxy-1-(4-{2-[2-hydroxy-3-(3-triethoxysilylpropylamino)propoxy]ethyl}phenyl)-2-methylpropan-1-one 2-Hydroxy-1-[4-(2-{2-hydroxy-3-[(2-hydroxy-3-{2-[4-(2-hydroxy-2-methylpropionyl)phenoxy]ethyl}propyl)-(3-triethoxysilylpropyl)amino]propoxy}ethyl)phenyl]-2-methylpropan-1-one

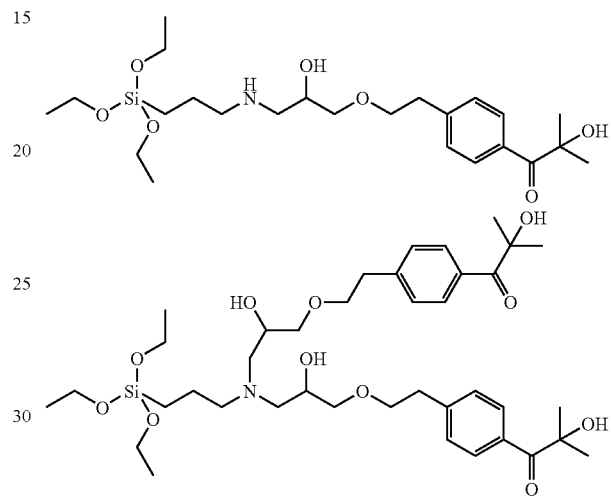

The procedure of Example 1B is repeated with the epoxide of 2-hydroxy-1-[4-(2-hydroxyethyl)phenyl]-2-methylpropan-1-one (see Example 15) to give a mixture of the title compounds.

Example 30

2-Hydroxy-1-(4-{2-[2-hydroxy-3-(2-hydroxyethylamino)propoxy]ethyl}phenyl)-2-methylpropan-1-one 2-Hydroxy-1-[4-(2-{2-hydroxy-3-[(2-hydroxyethyl)-(2-hydroxy-3-{2-[4-(2-hydroxy-2-methylpropionyl)phenoxy]ethyl}propyl)amino]propoxy}ethoxy)phenyl]-2-methylpropan-1-one

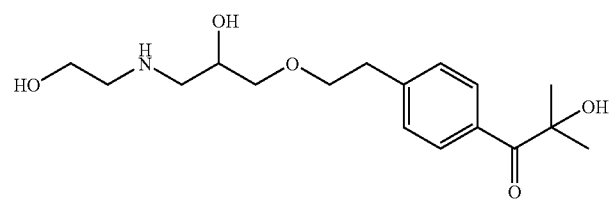

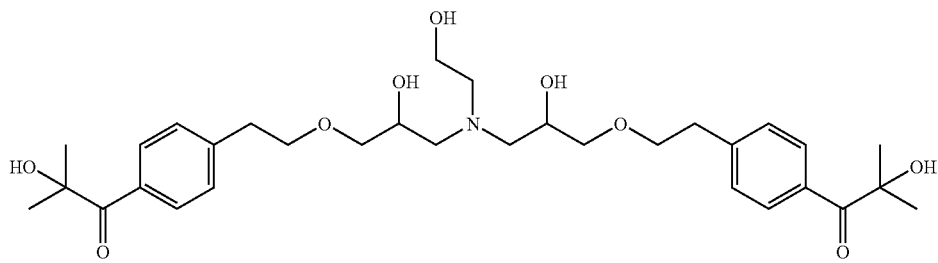
The procedure of Example 3 is repeated with 2-hydroxy-1-[4-(2-hydroxyethyl)phenyl]-2-methylpropan-1-one ethanolamine to give a mixture of the title compounds.
Example 31
3,3'-Bis-{2-[4-(2-hydroxy-2-methylpropionyl)phenyl]ethoxycarbonyl}biphenyl-4,4'-dicarboxylic acid
3,4'-Bis-{2-[4-(2-hydroxy-2-methylpropionyl)phenyl]ethoxycarbonyl}biphenyl-4,4'-dicarboxylic acid
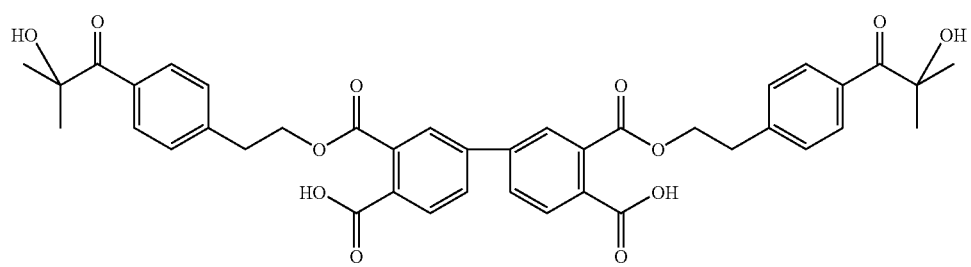
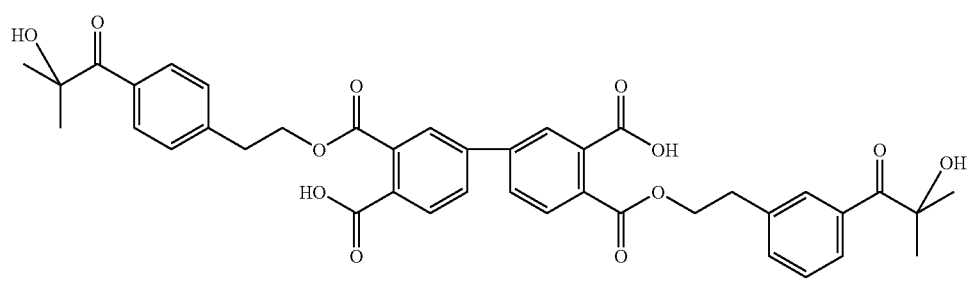

The procedure of Example 10 is repeated with 2-hydroxy-1-[4-(2-hydroxyethyl)phenyl-2-methylpropan-1-one (example 15) substituted for 2-hydroxy-1-[4-(2-hydroxyethoxy)phenyl-2-methylpropan-1-one to obtain a mixture of the title compounds.

Example 32

1-[4-(2-{3-[Bis-(3-silanyl-propyl)amino]-2-hydroxypropoxy}ethyl)phenyl]-2-hydroxy-2-methyl-propan-1-one

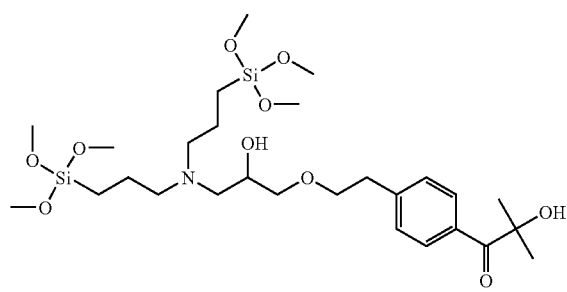 [SMILES: CO[Si](CCCN(CCC[Si](OC)(OC)OC)CC(O)COCCc1ccc(C(=O)C(C)(C)O)cc1)(OC)OC]

The procedure of example 2 is repeated with bis(triethoxysilylpropyl)amine substituted for diethanolamine to give the title compound.

Example 33

2-Hydroxy-2-(4-methoxybenzoyl)cyclohexanecarboxylic acid(3-silanyl-propyl)-amide

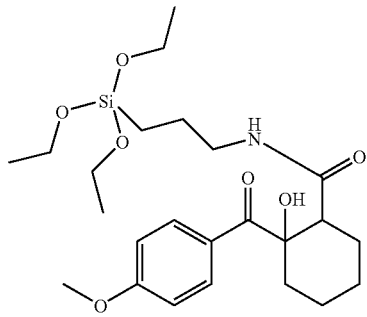 [SMILES: CCO[Si](CCCNC(=O)C1CCCCC1(O)C(=O)c1ccc(OC)cc1)(OCC)OCC]

3-Aminopropyltriethoxysilane (22.14 g, 0.100 mol) is added to a solution of 26.03 g (0.100 mol) of 6-(4-methoxy-benzoyl)-7-oxa-bicyclo[4.2.0]octan-8-one in methylene chloride. The reaction mixture is heated at reflux for several hours and monitored by thin layer chromatography. Upon completion of the reaction, solvent is evaporated to obtain the title compound.

Example 34

2-Hydroxy-2-(4-methoxy-benzoyl)cyclohexanecarboxylic acid bis(2-hydroxyethyl)amide

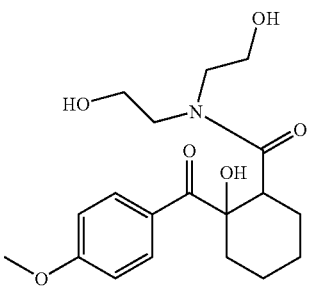 [SMILES: COc1ccc(C(=O)C2(O)CCCCC2C(=O)N(CCO)CCO)cc1]

A solution of 26.03 g (0.100 mol) of 6-(4-methoxy-benzoyl)-7-oxa-bicyclo[4.2.0]octan-8-one in 200 ml of methylene chloride is added to 10.5 g (0.100 mol) of diethanolamine and 32 ml of N,N-diisopropylethylamine. The reaction mixture is heated at reflux for several hours and monitored by thin layer chromatography. Upon completion of the reaction, the mixture is cooled and poured into 1N hydrochloric acid solution. The organic layer is washed with water, dried over anhydrous sodium sulfate, and concentrated to give the title compound.

Example 35

2-{2-[4-(2-hydroxy-2-methylpropionyl)phenoxy]ethyl}dihydrogen1,2,4-benzenetricarboxylate 1-{2-[4-(2-hydroxy-2-methylpropionyl)phenoxy]ethyl}dihydrogen1,2,4-benzenetricarboxylate

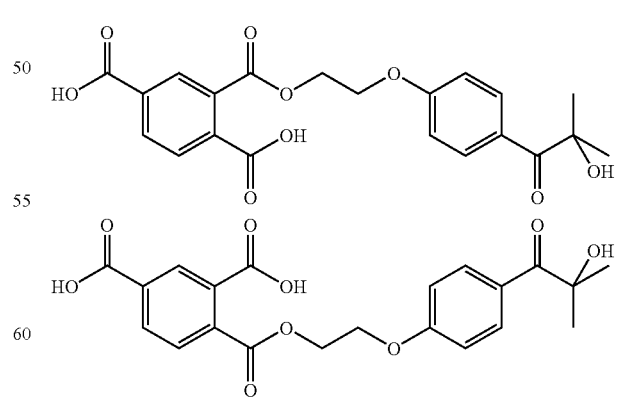

The procedure of Example 6 is repeated with 1,2,4-benzenetricarboxylic acid anhydride to give a mixture of the title compounds.

Example 36

2,4-Bis[{2-[4-(2-hydroxy-2-methyl-propionyl)phenoxy]ethyl}carbonyl]benzene-1,5-dicarboxylic acid 1,4-Bis[{2-[4-(2-hydroxy-2-methyl-propionyl)phenoxy]ethyl}carbonyl]benzene-1,5-dicarboxylic acid

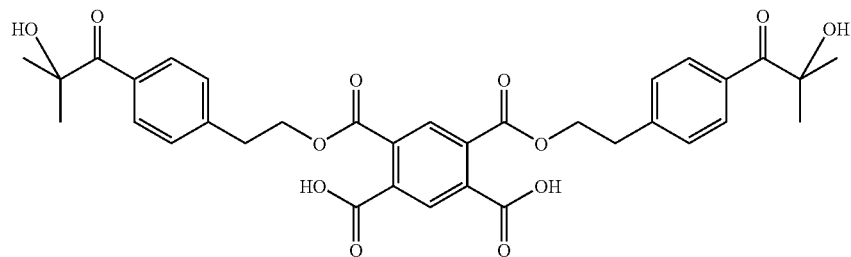

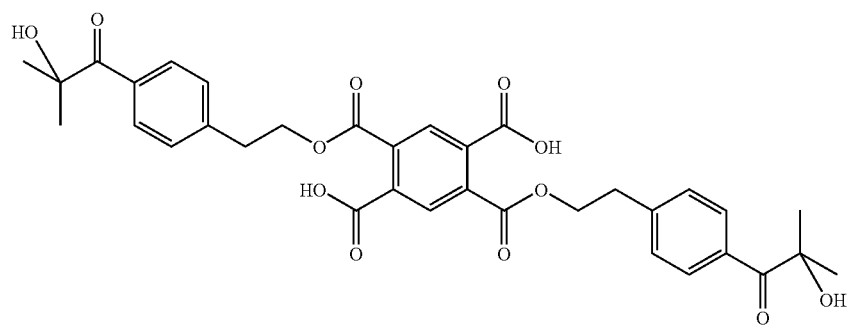

The procedure of Example 9 is repeated with 2-hydroxy-1-[4-(2-hydroxyethyl)phenyl-2-methylpropan-1-one (example 15) to give a mixture of the title compounds.

Example 37

2-{2-[4-(2-hydroxy-2-methylpropionyl)phenyl]ethyl}dihydrogen1,2,4-benzenetricarboxylate 1-{2-[4-(2-hydroxy-2-methylpropionyl)phenyl]ethyl}dihydrogen1,2,4-benzenetricarboxylate

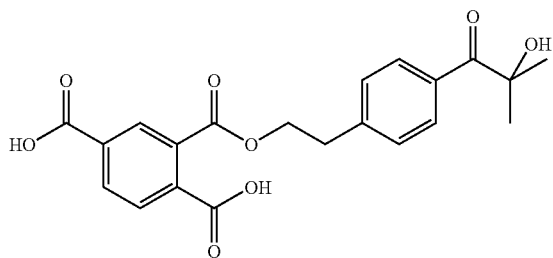

-continued

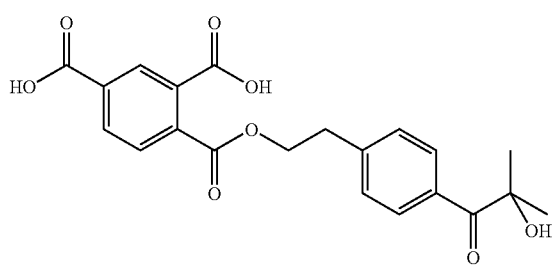

A mixture of the title compounds is prepared by from the reaction of 20.8 g (0.100 mol) of 2-hydroxy-1-[4-(2-hydroxyethyl)phenyl-2-methylpropan-1-one (Example 15), 18.2 g (0.0947 mol) of 1,2,4-benzenetricarboxylic anhydride and 7.5 g (0.0948 mol) of pyridine in 1,2-dimethoxyethane at 70° C. until the reaction is complete, followed by evaporation of the solvent.

Example 38

3,3'-Bis-{2-[4-((1-hydroxycyclohexyl)carbonyl)phenyl]ethoxycarbonyl}biphenyl-4,4'-dicarboxylic acid 4,3'-Bis-{2-[4-((1-hydroxycyclohexyl)carbonyl)phenyl]ethoxycarbonyl}biphenyl-3,4'-dicarboxylic acid 4,4'-Bis-{2-[4-((1-hydroxycyclohexyl)carbonyl)phenyl]ethoxycarbonyl}biphenyl-3,4'-dicarboxylic acid

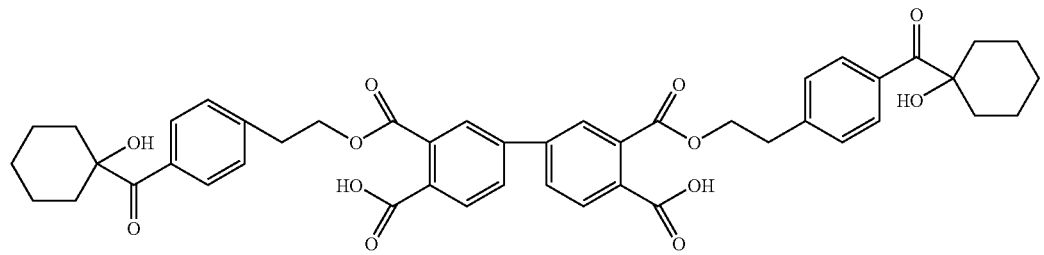

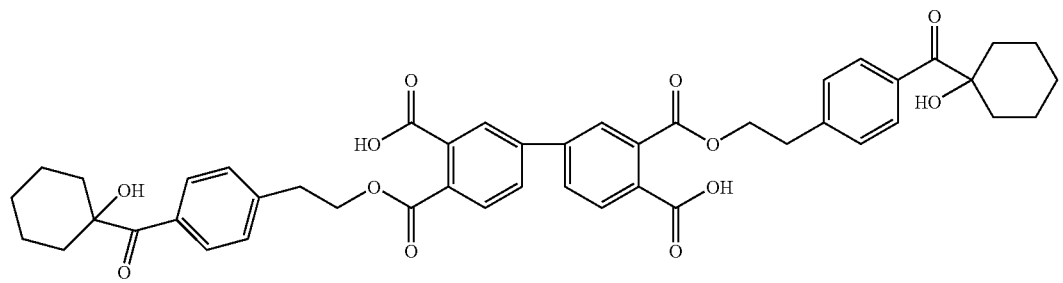

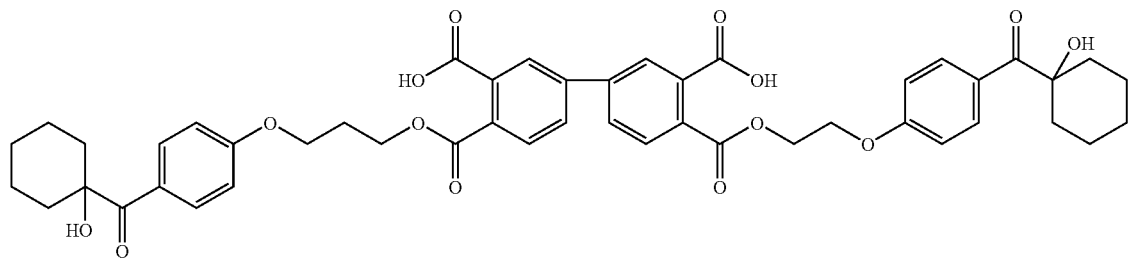

The reaction product, a mixture of three isomers, is obtained by stirring 4.96 g (20 mmol) of 4-(2-hydroxyethoxy)phenyl1-hydroxy-cyclohexyl ketone, 2.94 g (10 mmol) of 3,3',4,4'-biphenyltetracarboxylic dianhydride and 1.58 g (20 mmol) of pyridine in 80 ml of 1,2-dimethoxyethane at 80° C. until reaction is complete. Solvent is evaporated, the residue dissolved in 100 ml methylene chloride, washed with 100 ml 0.4N HCl, the organic layer concentrated and then dissolved in 200 ml ethyl acetate. The solution is washed with 170 ml water until pH 6, dried with MgSO$_4$, and solvent removed to give 5.87 g (74.2%) of a yellow-brown liquid: Mass spectrum: m/z 791.4 (M+H)$^+$.

Example 39

3,3'-Bis[{2-[4-((1-hydroxycyclohexyl)carbonyl)phenyl]ethoxy]carbony}lbenzophenone-4,4'-dicarboxylic acid 3,4'-Bis[{2-[4-((1-hydroxycyclohexyl)carbonyl)phenyl]ethoxy]carbonyl}benzophenone-4',3-dicarboxylic acid 4,4'-Bis[{2-[4-((1-hydroxycyclohexyl)carbonyl)pheny]ethoxy]carbonyl]benzophenone-3,3'-dicarboxylic acid

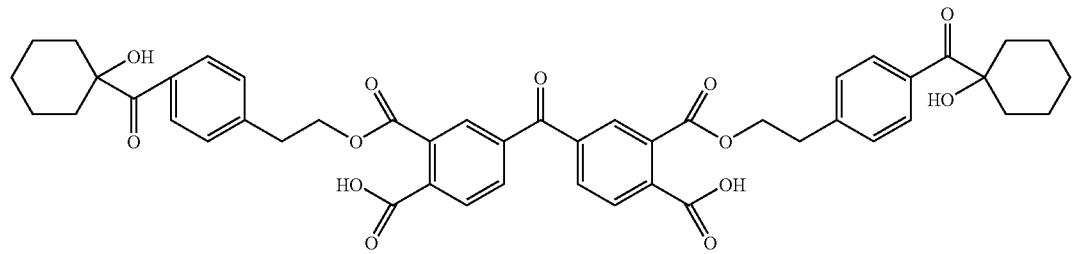

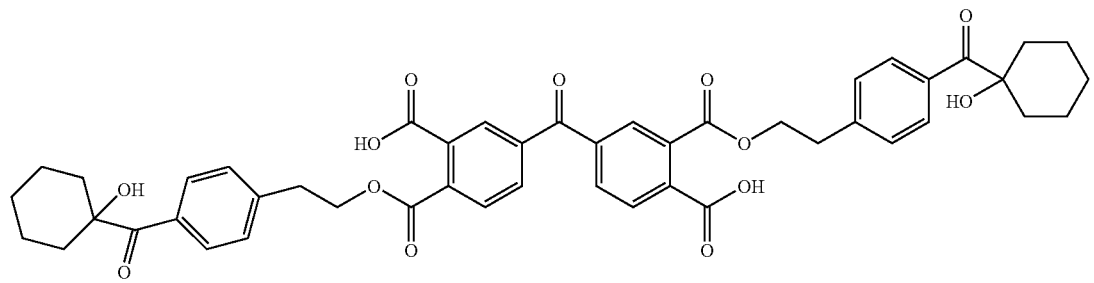

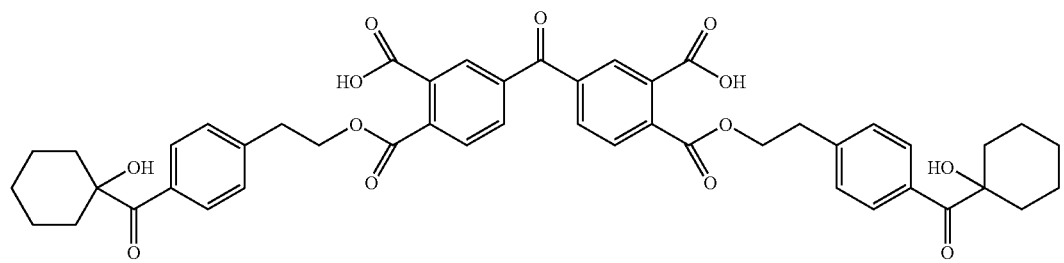

To 3,3'4,4'-benzophenonetetracarboxylic dianhydride (2.50 g, 7.75 mmol) and 4-(2-hydroxyethoxy)phenyl1-hydroxy-cyclohexyl ketone (3.70 g, 14.9 mmol) is added 50 ml of dimethoxyethane and pyridine (1.20 g, 15 mmol). The mixture is stirred at 50° C. until the reaction is complete by tlc. Solvent is evaporated and 100 ml ethyl acetate added to dissolve the residue, followed by successive washes with 80 ml 1.5N HCl solution and 80 ml water. The organic layer is dried with MgSO$_4$, filtered, and solvent removed to give 7.84 g light brown liquid: Mass spectrum: m/z 819 (M+H)$^+$

Example 40

3-[4-((1-hydroxycyclohexyl)carbonyl))phenyl]-3-phenylpropanoic acid

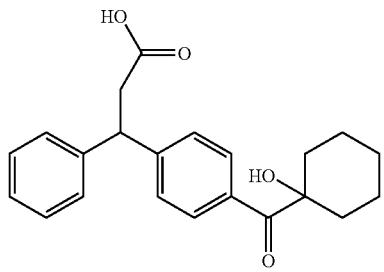 [SMILES: O=C(O)CC(c1ccccc1)c1ccc(C(=O)C2(O)CCCCC2)cc1]

Step 1: A mixture of 47 9 (0.20 mol) of methyl 3,3-diphenylpropanoate, 60 g (0.409 mol) of cyclohexanecarbonyl chloride, and 400 mol of 1,2-dichlorobenzene is cooled to 5° C. Aluminum chloride (104.5 g, 0.7836 mol) is added portionwise with stirring over 2 hours while the reaction temperature is kept between −5 and 8° C. The reaction is stirred within this temperature range for 20 hours, and then the reaction mixture is poured into a mixture of ice and concentrated hydrochloric acid (260 ml HCl+500 g ice), and stirred for 1 hour. The organic layer is washed twice with dilute hydrochloric acid and once with water, then concentrated under vacuum to give 98.59 grams of a light brown liquid, 48.05 g. of which is purified by column chromatography on silica gel, 8:2 heptane:ethyl acetate as eluent giving 11.02 g of methyl3-phenyl-3-[4-(cyclohexylcarbonyl)phenyl]propionate as a light brown liquid: Mass spectrum:m/z 351.2 (M+H)$^+$.

Step 2: A solution of 7.32 g (44.5 mmol) of bromine in 10 ml of methylene chloride is added dropwise at room temperature to a mixture of 10.18 g (37.10 mmol) of methyl3-phenyl-3-[4-(cyclohexylcarbonyl)phenyl]propionate in 250 ml of methylene chloride. The mixture is stirred for 16 hours at room temperature after which the reaction mixture is poured into a 5% aqueous sodium thiosulfate solution and stirred for 10 minutes. The organic layer is washed twice with 5% aqueous sodium thiosulfate solution, once with 10% sodium bicarbonate solution, dried over sodium sulfate, and concentrated to give 8.19.0 g (62.5%) of methyl3-phenyl-3-[4-((1-bromocyclohexyl)carbonyl)phenyl]propionate. Mass spectrum: m/z 429.1 (M+H)$^+$.

Step 3: A mixture of 8.19 g (23.2 mmol) of methyl3-phenyl-3-[4-((1-bromocyclohexyl)carbonyl)phenyl]propionate, 1.87 g (46.4 mmol) of sodium hydroxide, 10 ml of water, and 45 mL of 1,2-dimethoxyethane is heated at reflux for 16 hours. The reaction is concentrated and acidified with 25 ml of 1.5 N hydrochloric acid solution. Ethyl acetate (200 ml) is added, and the organic layer is washed with distilled water, dried over sodium sulfate, and concentrated. The crude product is passed through a pad of silica gel with ethyl acetate as the eluent to give 6.52 g of the title compound. Mass spectrum: m/z 353.2

Example 41

4-(2-Hydroxyethyl)phenyl1-hydroxy-cyclohexyl ketone

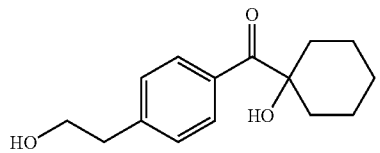 [SMILES: O=C(c1ccc(CCO)cc1)C1(O)CCCCC1]

Step 1: Four hundred milliliters of methylene chloride is cooled to 2° C., and then aluminum chloride (160 g, 1.20 mol) is added while the temperature is kept between −5 and 8° C. Cyclohexanecarbonyl chloride (75.08 g, 0.512 mol) is added dropwise to the solution. The reaction is kept within this temperature range with mechanical stirring for 45 minutes, and then 82.8 g, (0.505 mol) of 2-phenyl-ethyl acetate is added dropwise to the mixture, the temperature remaining between −5° C. to −8° C. The reaction is stirred within this temperature range for 20 hours, after which the reaction mixture is poured into a mixture of ice and concentrated hydrochloric acid (300 ml HCl+700 g ice), and stirred for 1 hour. The organic layer is washed with 2×250 ml water, dried, and concentrated under vacuum to give 116.12 g of a light brown liquid, 52.30 g of which is purified by column chromatography on silica gel with 7:3 heptane:ethyl acetate as the eluent giving 20.75 g of 4-(2-acetyloxyethyl)phenyl cyclohexyl ketone as a light brown liquid,: Mass spectrum: m/z 275.2 (M+H).

Step 2: A solution of 14.0 g (88 mmol) of bromine in 15 ml of methylene chloride is added dropwise at room temperature to a mixture of 12.0 g (43.7 mmol) of 4-(2-acetyloxyethyl)phenyl cyclohexyl ketone in 40 ml of methylene chloride. The mixture is stirred for 16 hours at room temperature then poured into a 5% aqueous sodium thiosulfate solution and stirred for 10 minutes. The organic layer is washed twice with 5% aqueous sodium thiosulfate solution, once with 10% sodium bicarbonate solution, dried over sodium sulfate, and concentrated to give 15.81.0 g of 4-(2-acetyloxyethyl)phenyl1-bromo-cyclohexyl ketone: Mass spectrum: m/z=353.25 (M+H)$^+$.

Step 3: A mixture of 8.19 g (23.2 mmol) of 4-(2-acetyloxyethyl)phenyl1-bromo-cyclohexyl ketone, 6.26g (15.65 mmol) of sodium hydroxide, 20 ml of water, and 50 ml of 1,2-dimethoxyethane is heated at reflux for 16 hours. The reaction is concentrated, and then acidified with 25 ml of 1.5 N hydrochloric acid. Ethyl acetate (200 ml) is added, and the organic layer is washed with distilled water, dried over sodium sulfate, and concentrated. The crude product is passed through a pad of silica gel with ethyl acetate as the eluant to give 5.50 g of the title compound which is further purified by recystallization. Mass spectrum: m/z=249 (M+H).

Example 42

A 5% w/w solution of photoinitiator is dissolved in a primer resin comprising 58% Ebecryl 8804, 14% HDODA and 28% IBOA. The resin is applied over unprimed steel panels, cleaned with alcohol prior to use, with a Bird bar at a wet thickness of 1.5 mil. Panels are passed under a single Fusion lamp (600 W, VPS, H-Bulb and/or V-Bulb) at a belt speed of 10 feet per minute.

Degree of cure is evaluated visually and by applying the mar test. Dry adhesion is determined by using 3M tape #10 and a standard cross-hatch tester with 2 mm razor spacing. The tape is pressed onto the cross-hatch pattern on the panel, then quickly pulled off. Adhesion is the ratio of squares where the coating has not been pulled off by the tape to the total number of squares, expressed as a percent. The cured panels are soaked in water at 22 degrees C. for 5 days. The panels are then rinsed in warm water and patted dry with a soft paper cloth. The cross-hatch test is performed to give wet adhesion data. Results are summarized in Table 1

TABLE 1

Adhesion data for exposed panels.

| Entry | Photoinitiator | con-centration | surface cure | % adhesion dry | % adhesion wet |
|---|---|---|---|---|---|
| 1 | PI 1 | 5 pph | not recorded | 35 | 15 |
| 2 | Example 23 | 5 pph | hard | 63 | 13 |
| 3 | Example 19 | 5 pph | tacky | 81 | 89 |
| 4 | Example 18 | 5 pph | hard | 83 | 22 |
| 5 | PI 2 | 5 pph | hard | 85 | 42 |
| 6 | PI 3 | 5 pph | hard | 65 | 47 |
| 7 | PI 4 | 5 pph | hard | 65 | 62 |
| 8 | Example 17 | 5 pph | hard | 87 | 33 |
| 9 | Example 17 | 5 pph | hard | 89 | 39 |
| 10 | Example 7 | 5 pph | hard | 89 | 85 |
| 11 | Example 19 | 5 pph | slight tack | 89 | 33 |
| 12 | PI 5 | 5 pph | hard | 92 | 79 |
| 13 | PI 6 | 5 pph | hard | 92 | 97 |
| 14 | Example 4 | 3.3 pph | hard | 94 | 31 |
| 15 | Example 19 | 5 pph | slight tack | 94 | 94 |
| 16 | Example 20 | 5 pph | tacky | 94 | 91 |
| 17 | Example 22 | 5 pph | tacky | 100 | 69 |
| 18 | Example 5 | 5 pph | slight tack | 100 | 99 |
| 19 | Example 6 | 5 pph | not recorded | 100 | 89 |

PI 1 is 20% by weight phenyl bis(2,4,6-trimethylbenzoyl)phosphine oxide and 80% by weight 2-hydroxy-2-methyl-1-phenyl-1-propanone
PI 2 is Bis-[4-(2-hydroxy-2-methylpropionyl)phenyl]methane
PI 3 is 70% oligo [2-hydroxy-2-methyl-1-[4-(1-methylvinyl)phenyl]propanone]and 30% 2-hydroxy-2-methyl-1-phenyl propan-1-one
PI 4 is 1-[-(4-benzoylphenylsulfanyl)phenyl]-2-methyl-2-(4-methylphenylsulfonyl)propan-1-one
PI 5 is 2-hydroxy-1-[4-(2-hydroxy-ethoxy)phenyl]-2-methylpropan-1-one
PI 6 is 50 weight % benzophenone and 50% weight % 1-hydroxycyclohxyl phenyl ketone

What is claimed:

1. A coated metal surface which comprises
a) a metal of steel or aluminum with at least one surface which is immediately adjacent to a coating layer obtained by photocuring a coating composition comprising
b) one or more ethylenically unsaturated monomers, oligomers or prepolymers, and
c) from about 0.05 to about 25% by weight, based on the total weight of the coating layer solids, of one or more compounds selected from the group consisting of

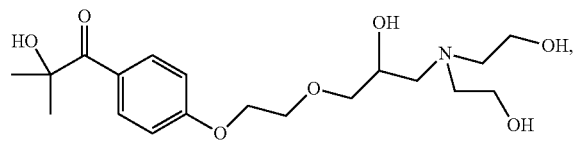

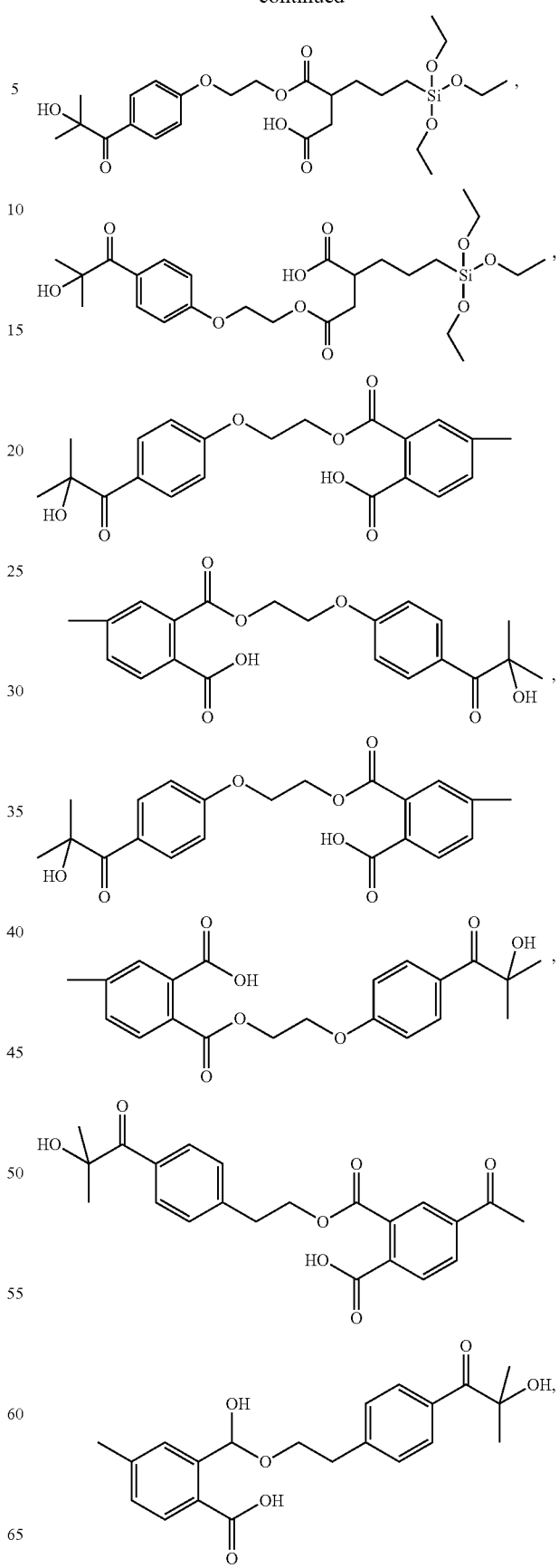

-continued

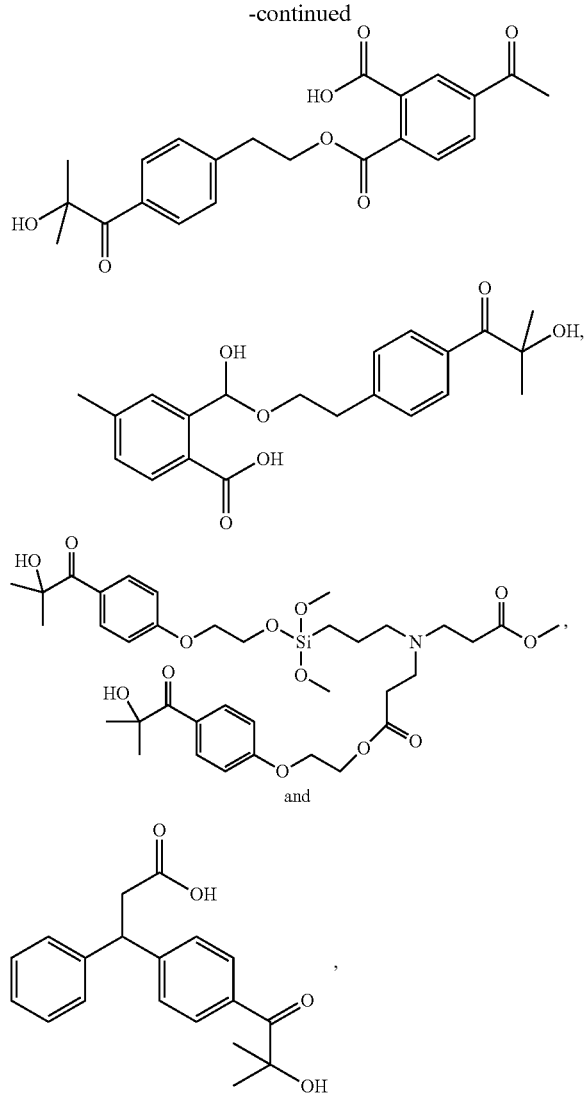

wherein the coating layer is cured under a light with wavelength from about 200 nm to about 450 nm.

2. A coated metal surface according to claim 1, wherein component b) comprises one or more acrylate monomers, oligomers or prepolymers.

3. A coated metal surface according to claim 1 which also comprises 5-25 weight percent, based on total solids, of an additional photoinitiator or photoinitiator blend.

4. A coated metal surface according to claim 3, wherein the additional photoinitiator or photoinitiator blend comprises one or more compounds selected from the group consisting of phenyl bis(2,4,6-trimethylbenzoyl)phosphine oxide, 2-hydroxy-2-methyl-1-phenyl-1-propanone, 2-Hydroxy-1-{4-[4-(2-hydroxy-2-methylpropionyl)benzyl]phenyl}-2-methyl-propan-1-one, 2-Hydroxy-1-[4-(2-hydroxyethoxy)phenyl]-2-methylpropan-1-one, benzophenone and 1-hydroxycyclohexyl phenyl ketone.

5. A coated metal surface according to claim 4, wherein the additional photoinitiator or photoinitiator blend comprises one or more compounds or blends selected from the group consisting of
   a blend of 20% by weight phenyl bis(2,4,6-trimethylbenzoyl)phosphine oxide and 80% by weight 2-hydroxy-2-methyl-1-phenyl-1-propanone;
   2-Hydroxy-1-{4-[4-(2-hydroxy-2-methylpropionyl)benzyl]phenyl}-2-methylpropan-1-one;
   2-Hydroxy-1-[4-(2-hydroxyethoxy)phenyl]-2-methylpropan-1-one;
   a blend of 50 weight % benzophenone and 50 weight % 1-hydroxycyclohexyl phenyl ketone;
   Phenyl bis(2,4,6-trimethylbenzoyl)phosphine oxide;
   1-Hydroxycyclohexyl phenyl ketone; and
   2-Hydroxy-2-methyl-1-phenyl propan-1-one.

6. A coated metal surface according to claim 3, wherein the additional photoinitiator or photoinitiator blend comprises the blend 50 weight % benzophenone and 50 weight % 1-hydroxycyclohexyl phenyl ketone or the compound phenyl bis (2,4,6-trimethylbenzoyl)phosphine oxide.

\* \* \* \* \*